(12) United States Patent
DeVoe et al.

(10) Patent No.: US 11,786,899 B2
(45) Date of Patent: Oct. 17, 2023

(54) TRAP ARRAYS FOR ROBUST MICROFLUIDIC SAMPLE DIGITIZATION

(71) Applicant: University of Maryland, College Park, College Park, MD (US)

(72) Inventors: Don L. DeVoe, Bethesda, MD (US); Alex Sposito, Arlington, VA (US)

(73) Assignee: University of Maryland, College Park, College Park, MD (US)

( * ) Notice: Subject to any disclaimer, the term of this patent is extended or adjusted under 35 U.S.C. 154(b) by 153 days.

(21) Appl. No.: 15/887,676

(22) Filed: Feb. 2, 2018

(65) Prior Publication Data

US 2018/0214873 A1   Aug. 2, 2018

Related U.S. Application Data

(60) Provisional application No. 62/514,501, filed on Jun. 2, 2017, provisional application No. 62/453,763, filed on Feb. 2, 2017.

(51) Int. Cl.
*C12Q 1/686* (2018.01)
*B01L 3/00* (2006.01)
*B01L 7/00* (2006.01)

(52) U.S. Cl.
CPC ..... *B01L 3/502753* (2013.01); *B01L 3/50273* (2013.01); *B01L 7/52* (2013.01); *C12Q 1/686* (2013.01); *B01L 2200/027* (2013.01); *B01L 2200/0605* (2013.01); *B01L 2200/12* (2013.01); *B01L 2300/0645* (2013.01); *B01L 2300/0816* (2013.01); *B01L 2300/0819* (2013.01); *B01L 2300/0858* (2013.01); *B01L 2300/0864* (2013.01); *B01L 2300/0893* (2013.01);

(Continued)

(58) Field of Classification Search
CPC .......... B01L 3/50273; B01L 2300/069; B01L 2400/0406; B01L 2200/027; B01L 2200/0605; B01L 2200/0673; B01L 2300/0816; B01L 2300/0864; B01L 7/52; C12Q 1/686

See application file for complete search history.

(56) References Cited

U.S. PATENT DOCUMENTS 5,643,764 A * 7/1997 Kosak ............... C12Q 1/68
                                                       435/174
6,908,594 B1 6/2005 Schaevitz et al.
(Continued)

FOREIGN PATENT DOCUMENTS

JP   2009-178167 A   8/2009
WO   2016/209943 A1  12/2016

*Primary Examiner* — Young J Kim
(74) *Attorney, Agent, or Firm* — Rothwell, Figg, Ernst & Manbeck, P.C.

(57) ABSTRACT

A microfluidic device including at least one channel in fluid communication with a sample trap array. Specifically, the configuration and geometry of the trap arrays according to the present invention allows for performing sample digitization that supports passive self-discretization within the sample traps without the need for any external flow control or actuation. Geometrical parameters defining the sample traps, including the trap width and the trap depth, are selected to optimize self-filling of the sample traps. Reagents are incorporated into the sample traps during device fabrication to allow for performing multiplexed reactions within the sample traps.

19 Claims, 22 Drawing Sheets
(18 of 22 Drawing Sheet(s) Filed in Color)
Specification includes a Sequence Listing.

(52) U.S. Cl.
CPC .................. *B01L 2400/0406* (2013.01); *B01L 2400/0688* (2013.01)

(56) References Cited

U.S. PATENT DOCUMENTS

| | | | |
|---|---|---|---|
| 7,238,324 B2* | 7/2007 | Ko | B01L 3/502707 422/505 |
| 7,682,565 B2 | 3/2010 | Linton et al. | |
| 2003/0138829 A1 | 7/2003 | Unger et al. | |
| 2005/0089863 A1* | 4/2005 | Karlsen | B01L 3/50273 435/6.19 |
| 2007/0014695 A1* | 1/2007 | Yue | B01L 3/502707 422/400 |
| 2009/0186357 A1 | 7/2009 | Mauk et al. | |
| 2011/0311394 A1 | 12/2011 | Worsman et al. | |
| 2012/0164036 A1 | 6/2012 | Stern et al. | |
| 2013/0130232 A1* | 5/2013 | Weibel | G01N 33/54386 435/5 |
| 2013/0338194 A1* | 12/2013 | Mukherjee | A61B 18/12 514/331 |
| 2014/0027284 A1 | 1/2014 | McKee et al. | |
| 2014/0349279 A1 | 11/2014 | Berthelot et al. | |
| 2015/0090674 A1* | 4/2015 | Lee | A61B 5/6866 210/797 |
| 2015/0352552 A1 | 12/2015 | Levenberg et al. | |
| 2016/0279634 A1 | 9/2016 | Stemme et al. | |

* cited by examiner

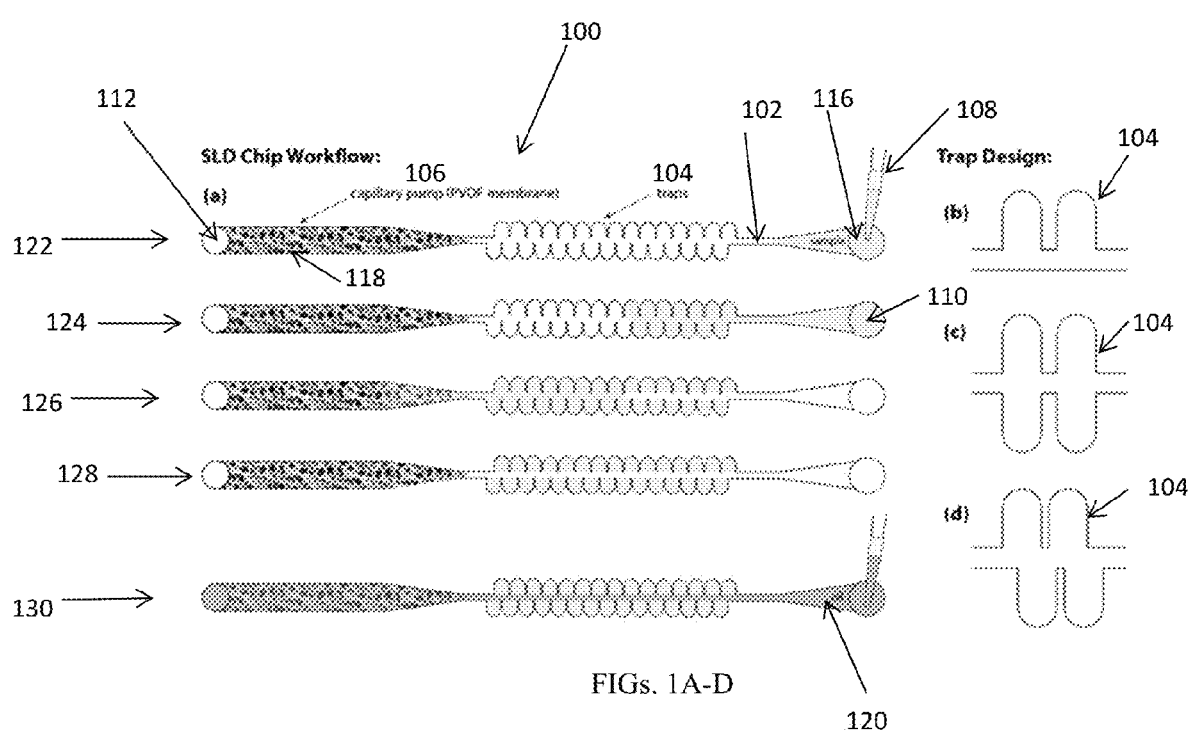
FIGs. 1A-D

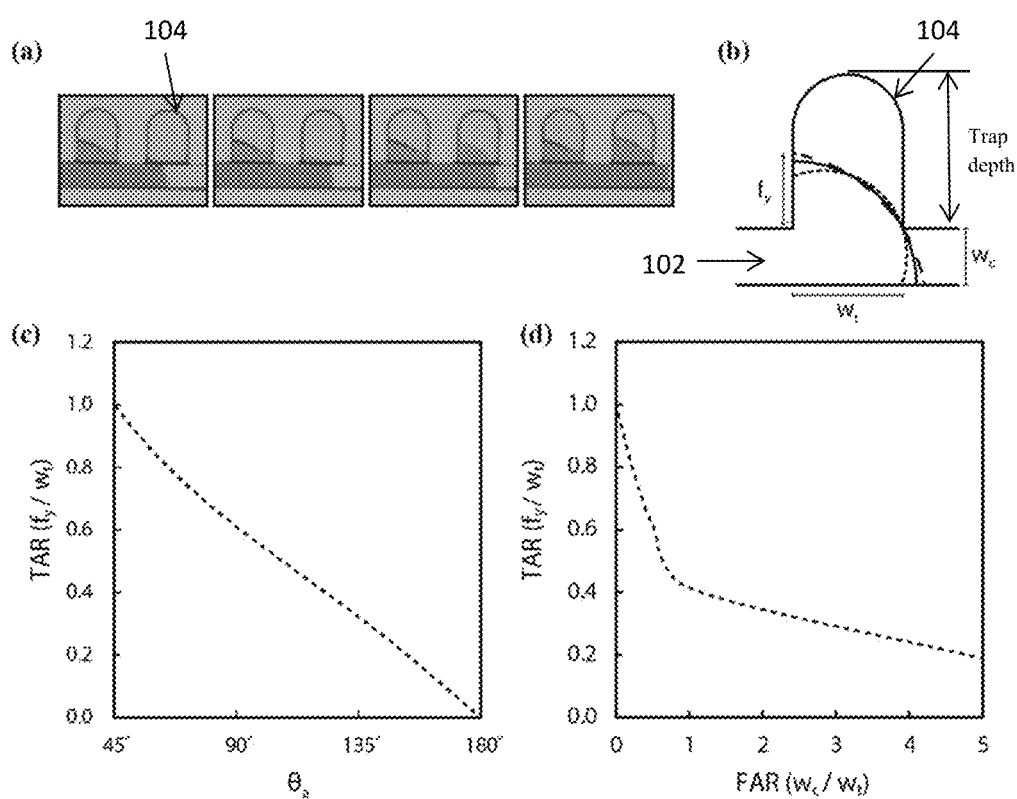
FIGs. 2A-D

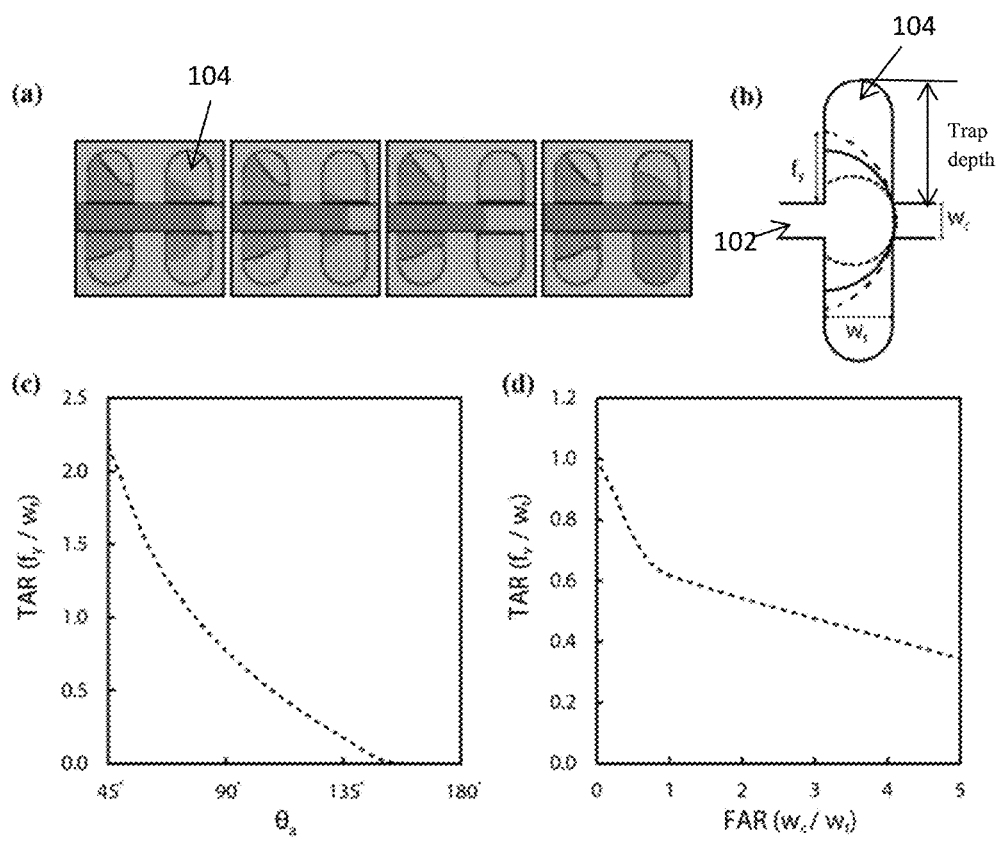
FIGs. 3A-D

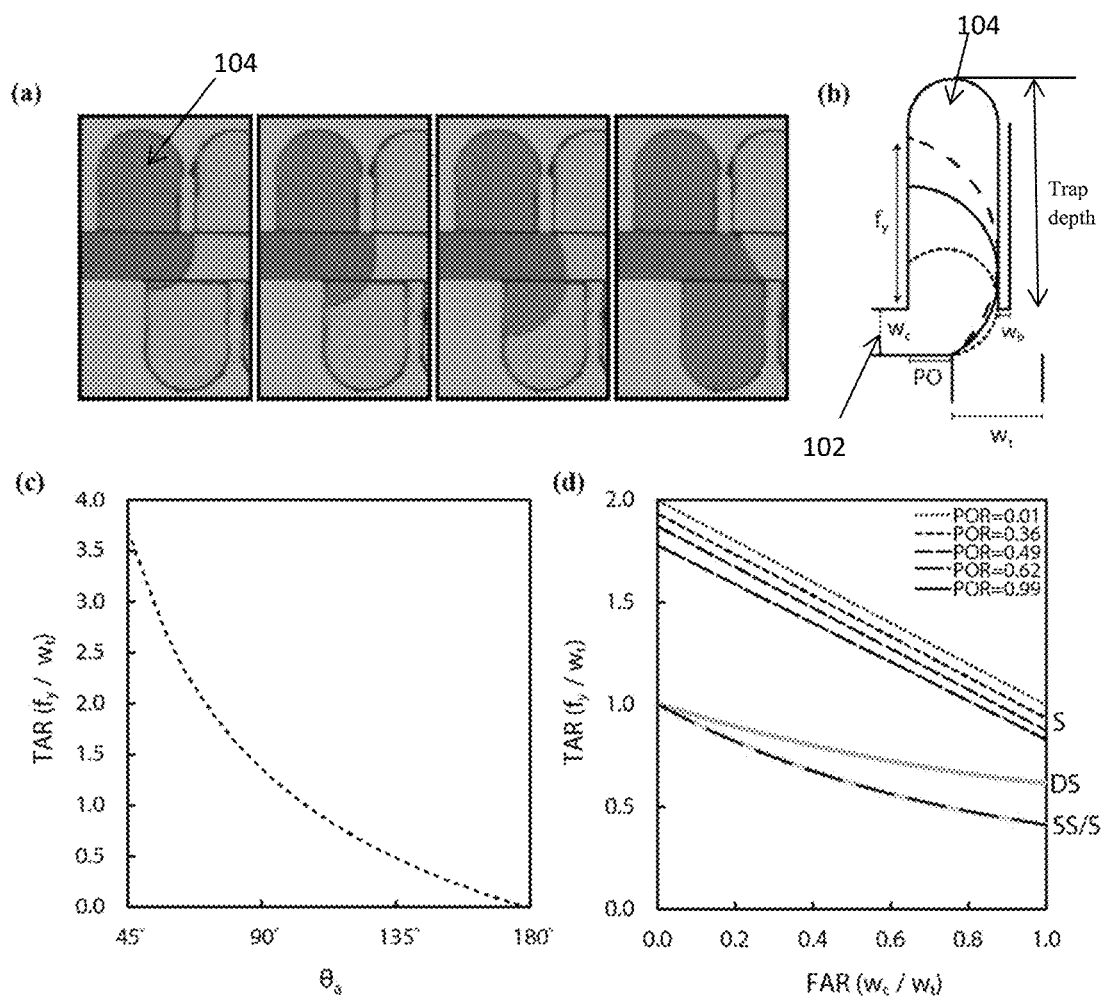
FIGs. 4A-D

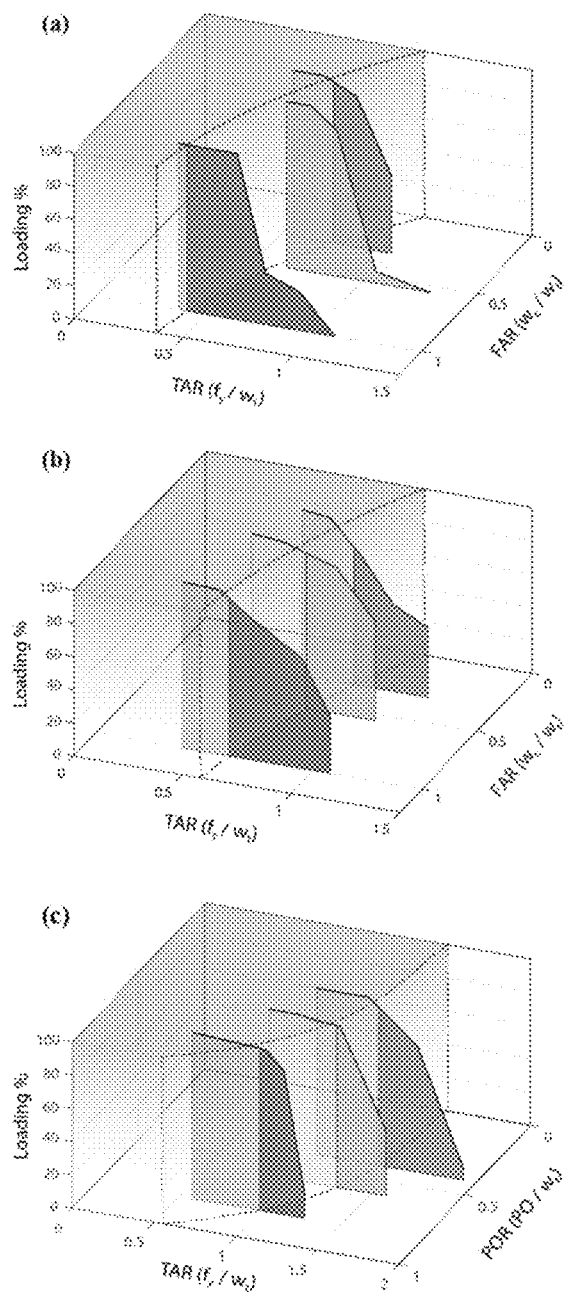
FIGs. 6A-C

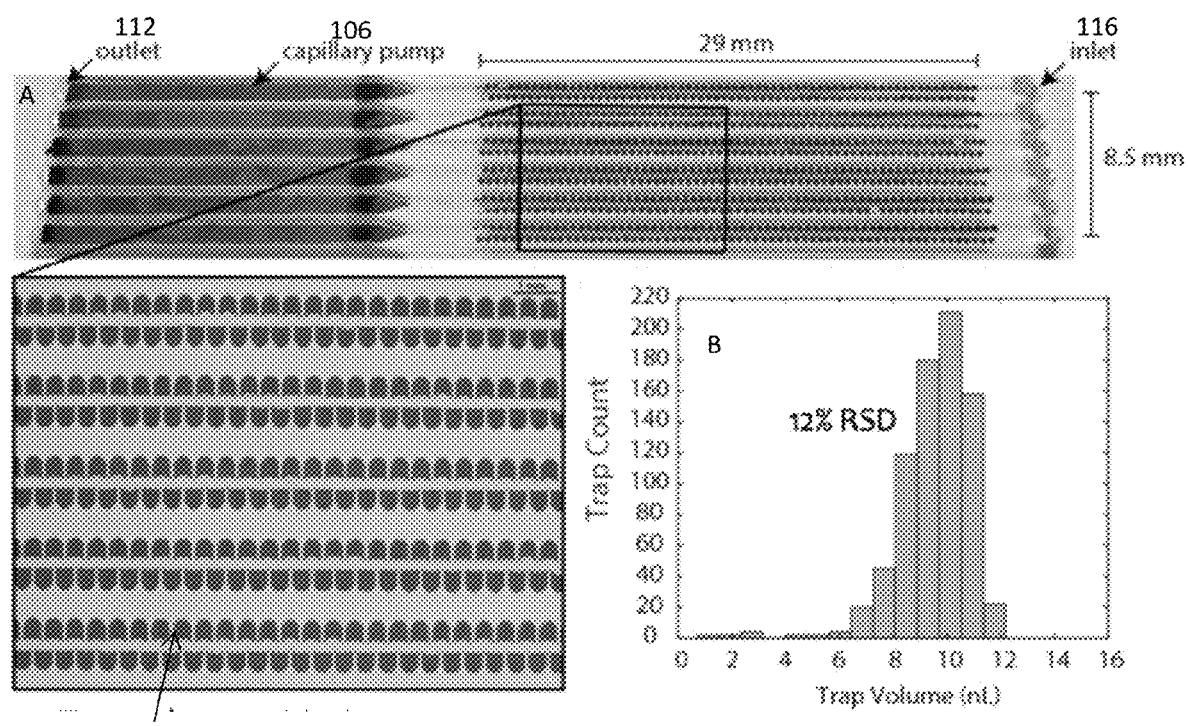
FIGs. 7A-B

FIGs. 10A-C

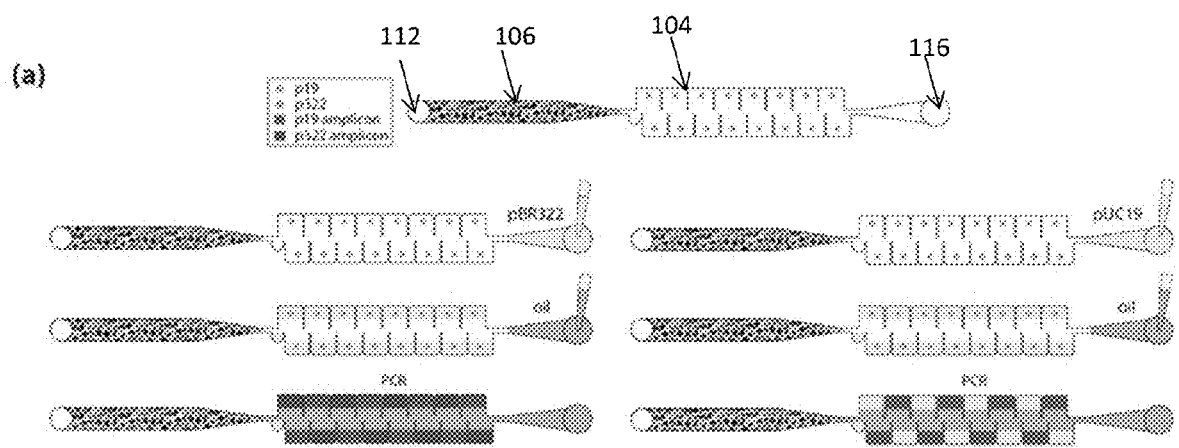
FIGs. 12A-B

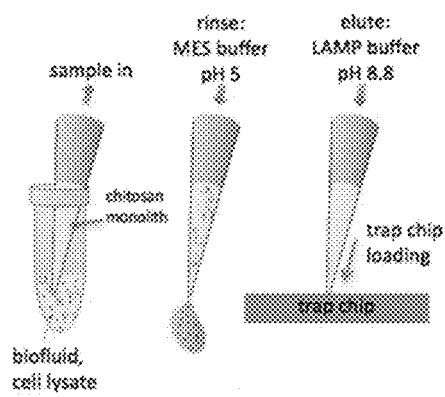
FIGs. 13A-C
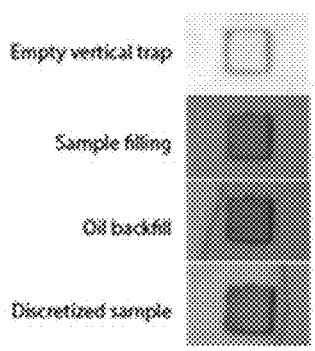
FIG. 14

TRAP ARRAYS FOR ROBUST MICROFLUIDIC SAMPLE DIGITIZATION

INCORPORATION BY REFERENCE

This application claims the benefit of priority to U.S. Provisional Patent Application Ser. Nos. 62/514,501, filed on Jun. 2, 2017, and 62/453,763, filed on Feb. 2, 2017, which are incorporated herein by reference in their entireties.

The present application includes a Sequence Listing filed in electronic format. The Sequence Listing is entitled "3400-327_ST25.txt" created on Feb. 2, 2018, and is 2,000 bytes in size. The information in the electronic format of the Sequence Listing is part of the present application and is incorporated herein by reference in its entirety.

BACKGROUND OF THE INVENTION

Field of the Invention

The present invention relates to a device for performing passive microfluidic sample digitization without the need for any external flow control or actuation. Furthermore, the device according to the present invention can be used for multiplexed amplification reactions.

Description of Related Art

Sample digitization, or the segregation of sample volume into smaller parts, is an important operation required in many applications for genomics, clinical diagnostics, and drug discovery. The conventional approach to forming an array of discrete fluid volumes from an initial sample solution has been to rely on robotic fluidic handling. However, this approach requires cumbersome and costly equipment, suffers from unfavorable scaling in multistep assays, and is generally restricted to discretized sample volumes in the microliter range. Moreover, the need for an open substrate such as a microwell plate for deposition increases the risk of external contamination, introduces the need to limit sample evaporation, and constrains the types of assay operations that may be performed.

A variety of microfluidic technologies have been developed to enable automated sample digitization within enclosed flow systems. One of the most common approaches to microfluidic digitization is droplet generation, an active digitization process wherein a sample volume is dispersed within an immiscible phase to create small uniform reactors defined by individual droplets. Microfluidic droplet generators allow the flow rates of the continuous and dispersed phases to be adjusted for control over the volume and production rate of the digitized sample volumes, and can be readily used for the formation of high density arrays. However, droplet generation is an active digitization method requiring continuous and precise flow control for monodispersed droplet formation, necessitating the use of fluidic interfacing and flow control hardware, thereby increasing the complexity and cost of the final device. Furthermore, because of the active nature of the droplet generation process, the resulting droplets typically require additional mechanisms downstream for manipulation and assay analysis. While a range of methods for downstream control via droplet trapping and release using hydrodynamic, by optical or acoustic manipulation have been explored, these added operations can degrade the potential for simplicity, affordability, and integration offered by microfluidics.

Electrowetting-on-dielectric (EWOD) represents an alternative active digitization technique that enables on-demand formation of discrete sample volumes together with controlled manipulation of individual droplets for subsequent assay operations. In the EWOD technology, differential capillary forces are generated across a droplet by controlling the surface contact angle between the droplet and an underlying substrate through application of an external electric potential, allowing sample packets to be segregated and transported by direct voltage control. Despite this unique functionality, EWOD devices can present challenges in scalability related to electrode addressing, demand high voltages for operation, and require relatively complex fabrication methods to define both the dielectric and electrode layers needed for reliable device operation.

Driven by the need for simpler and more robust methods of sample discretization, a number of passive digitization methods have been developed. Passive sample digitization takes advantage of processes that do not require precise control over fluid flow or the use of active control elements, such that discrete volumes are created on-chip automatically within spatially indexed locations. A central advantage of these passive methods over active digitization is that the instrumentation required for compartmentalization is greatly reduced or eliminated, making these techniques very well suited for use in devices where low cost and simple operation are important considerations.

The passive sample digitization concept has been successfully applied to various open fluidic platforms in which sample is discretized within arrays of patterned microwells by sequential well priming and selective dewetting of the surrounding field while leaving individual fluid volumes anchored within the wells. Similarly, selective patterning of hydrophilic regions or porous absorbent materials within wells on a hydrophobic surface has been employed to initiate wetting in specific locations while allowing excess sample to be easily removed.

A related method has been applied to sealed microfluidic systems, allowing the passive discretization of sample in enclosed microchannels. While various device geometries have been explored, they share a similar approach in which sample is introduced through a microchannel by pressure driven flow, vacuum, or centrifugal actuation to prime a series of wells fluidically connected to one of the microchannel walls, followed by the introduction of an immiscible oil phase to remove residual sample from the microchannel. The oil flow serves to shear off sample from the filled wells, leaving digitized aqueous fluid volumes behind. The oil phase used to backfill the chip also serves to fully isolate the sample volumes and prevent evaporation. In these devices, polydimethylsiloxane (PDMS) is commonly chosen as a substrate material due to its high air permeability, enabling dead-end filling of the wells without trapping air bubbles during priming. The devices are also typically filled with an oil phase prior to sample introduction, thereby enhancing the filling of aqueous sample into hydrophobic PDMS wells, and improving sample retention during the final oil backfill. Accordingly, a new approach to sample digitization that supports passive self-discretization without any external flow control or actuation is needed.

Multiplex PCR (mPCR) is an approach to increasing the throughput of nucleic acid analysis by allowing the amplification and detection of multiple sequence targets in a single PCR reaction. For example, mPCR has been widely applied to the analysis of antibiotic-resistance genes from bacterial samples, with a range of mPCR assays developed for identification of antibiotic-resistant enterobacteriaceae, enterococci, *Vibrio cholerae*, and *S. aureus*. However, complexity of primer design and validation for mPCR remains a significant limitation for new assay development. More fundamentally, primer competition constrains multiplexing depth, with 5-plex assays representing the nominal maximum, and spectral overlap of fluorescent probes used in real-time PCR (qPCR) further limits the number of amplicons that may be detected in a single reaction. A sequential mPCR approach involving a series of individual microliter-volume mPCR reactions using different primer sets has recently emerged, but at the expense of assay time.

As an alternative to mPCR, multiplexing may be achieved by performing multiple individual PCR reactions in an array of spatially-isolated reaction wells. Commercially available microwell plate platforms supporting multiplexed PCR with integrated reagents have been developed, but are limited by high consumable costs and the need for complex instrumentation for system operation. Several microfluidic technologies have been explored to address these constraints, by reducing reagent and infrastructure requirements while enabling semi-automated assay operation. Approaches include the use of centrifugal microfluidics where centrifugal actuation is used to actively deliver sample to on-chip reaction chambers containing specific PCR primer sets, and reconfigurable microfluidic devices where isolated primer sets on one substrate are combined with individual reaction chambers on a second substrate through relative motion between the chip elements. However, these approaches still rely on significant supporting equipment for operation.

Accordingly, there is a need for a low cost microfluidic platform designed to perform highly scalable multiplexed PCR with minimal manual input.

SUMMARY OF THE INVENTION

The present invention relates to microfluidic devices including a sample trap (also referred to as sample well) array. Specifically, the configuration and geometry of the trap arrays according to the present invention allows for performing sample digitization that supports passive self-discretization within the sample traps without the need for any external flow control or actuation.

In one aspect of the invention, a self-loading microfluidic device and a method for loading the microfluidic device are provided. Specifically, the microfluidic device comprises a substrate having at least one microfluidic channel provided therein. In one embodiment, the substrate is fabricated from a thermoplastic polymer. The microfluidic channel is in fluid communication with inlet and outlet ports. A sample is introduced into the microfluidic channel through the inlet port. Furthermore, the microfluidic device includes a plurality of sample traps branching off the microfluidic channel. Each of the plurality of traps has geometrical parameters selected to optimize loading of the sample traps with the sample. A capillary pump in fluid communication with the microfluidic channel is configured to remove an excess sample from the microfluidic channel. An immiscible phase is loaded into the microfluidic channel to fully isolate each sample trap after an excess sample is removed from the microfluidic channel. A sealing layer is bonded to the thermal substrate. Furthermore, each sample trap includes reagents integrated into the microfluidic device during fabrication to perform a different reaction within each sample trap.

In yet another aspect of the present invention, a method for fabricating a self-loading microfluidic device is provided. Specifically, at least one microfluidic channel and microfluidic features are provided in a substrate. In one embodiment, the substrate is fabricated from a thermoplastic polymer. The microfluidic features include a chamber, an inlet port, an outlet port, and sample traps branching off the microfluidic channel. The microfluidic channel connects the inlet port to the chamber with the sample traps positioned in between. Next, at least one absorbent membrane is inserted into the chamber to remove an excess sample from the microfluidic channel. The thermoplastic substrate is mated to a sealing layer affixed to a spotting stage to seal the at least one microfluidic channel and the sample traps. In one embodiment, reagents are deposited on the sealing layer. Finally, a pressure is applied to bond the sealing layer to the substrate. In one embodiment, the method further comprises depositing reagents to the sealing layer prior to bonding it to the thermoplastic substrate. By way of example and without limitation, the reagents may be deposited to the sealing layer by a pin spotting tool through contact printing.

In yet another aspect of the invention, a device including a USB shell is provided. The USB shell comprises a self-loading chip having a sample trap array, electrodes patterned on a backside of the self-loading chip to sense the temperature, a LED array in optical communication with the self-loading trap array, a CMOS imager to perform fluorescence imaging of the trap array, and a routing board to control the amplification of target nucleic acids in a biological sample.

The self-loading chip comprises a substrate having at least one microfluidic channel provided therein. In one embodiment, the substrate is fabricated from a thermoplastic polymer. A sample is introduced into the microfluidic channel through an inlet port. A plurality of sample traps comprising reagents branches off the microfluidic channel. A capillary pump is in fluid communication with the channel and an outlet port. The capillary pump is configured to remove an excess sample from the microfluidic channel prior to filling the microfluidic channel with an immiscible phase to isolate the sample traps.

In one embodiment, each sample trap includes reagents integrated into the microfluidic device during fabrication to perform a different biological reaction within each sample trap. In one embodiment, the reagents are encapsulated into a paraffin wax ensuring that the reagents remain encapsulated during sample loading. The primers are released from the paraffin wax by temperature application prior to performing the biological reaction.

In one embodiment of the present invention, the sample traps are lateral protrusions branching off from the same side or from the both sides (with or without centerline offset) of the microfluidic channel. In yet another embodiment, the sample traps are vertical traps beneath the microfluidic channel. In one embodiment, the microfluidic features, including a channel, inlet/outlet ports, sample traps, and a chamber, are milled in the thermoplastic substrate. Alternatively, the microfluidic features may be created on the thermoplastic substrate in a two-step embossing process.

By way of example and without limitation, the sample trap may have dimensions of 900 µm square and 250 µm deep. In yet another embodiment, the sealing layer is a thin film, which in one embodiment has a thickness of 200 µm.

In one embodiment, the capillary pump is a fabricated absorbent membrane, which in one embodiment is fabricated from a polyvinylidene fluoride (PVDF). The substrate may be fabricated from cyclic olefin polymer (COP). The sample may be injected into the inlet port by a pipette.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate various embodiments of the subject matter of this disclosure. In the drawings, like reference numbers indicate identical or functionally similar elements. Additionally, the left-most digit(s) of a reference number identifies the drawing in which the reference number first appears.

FIG. 1A illustrates a workflow and structural elements of a self-loading and digitizing (SLD) device.

FIG. 1B illustrates a single sided trap configuration on an SLD device.

FIG. 1C illustrates a double sided trap configuration on an SLD device.

FIG. 1D illustrates a staggered trap configuration on an SLD device.

FIG. 2A illustrates a sample loading process on an SLD device having a single sided trap configuration.

FIG. 2B illustrates a geometric representation for the single sided trap configuration at the instant the flow front touches the opposite trap wall at varying advancing front angle θa.

FIG. 2C illustrates trap aspect ratio (TAR) dependence on advancing front angle θa for the SLD device of FIG. 2A having a single sided trap configuration.

FIG. 2D illustrates TAR dependence on fluidic aspect ratio (FAR) for the SLD device of FIG. 2A having a single sided trap configuration.

FIG. 3A illustrates a sample loading process for an SLD device having a double sided trap configuration.

FIG. 3B illustrates a geometric representation for the double sided trap configuration at the instant the front touches the opposite trap wall at varying advancing front angle θa.

FIG. 3C illustrates TAR dependence on advancing front angle θa for the double sided SLD device.

FIG. 3D illustrates TAR dependence on FAR for the double sided SLD device.

FIG. 4A illustrates a loading process for an SLD device having a staggered trap configuration.

FIG. 4B illustrates a geometric representation for the staggered trap configuration at the instant the flow front touches the opposite trap wall at varying advancing front angle θa.

FIG. 4C illustrates TAR dependence on advancing front angle θa for the SLD device of FIG. 4A having a staggered trap configuration.

FIG. 4D illustrates TAR dependence on FAR for the SLD device of FIG. 4A having a staggered trap configuration.

FIG. 6A illustrates the design space for the single sided configuration.

FIG. 6B illustrates the design space for the double sided configuration.

FIG. 6C illustrates the design space for the staggered configuration.

FIG. 7A is an image of an SLD chip having a trap array according to one embodiment of the present invention.

FIG. 7B is a histogram of volume distribution in the loaded SLD device of FIG. 7A.

FIG. 12A illustrates an experimental design of the two step multiplex assay on the SLD platform.

FIG. 12B is a table of experimental results with pUC19 and pBR322 template loaded chips.

FIGS. 13A-13C illustrate a pipette-based sample preparation decoupling the purification and concentration of nucleic acids from the trap chip operation.

FIG. 14 illustrates filling process for an SLD device having vertical traps.

DETAILED DESCRIPTION

Figure 2F:
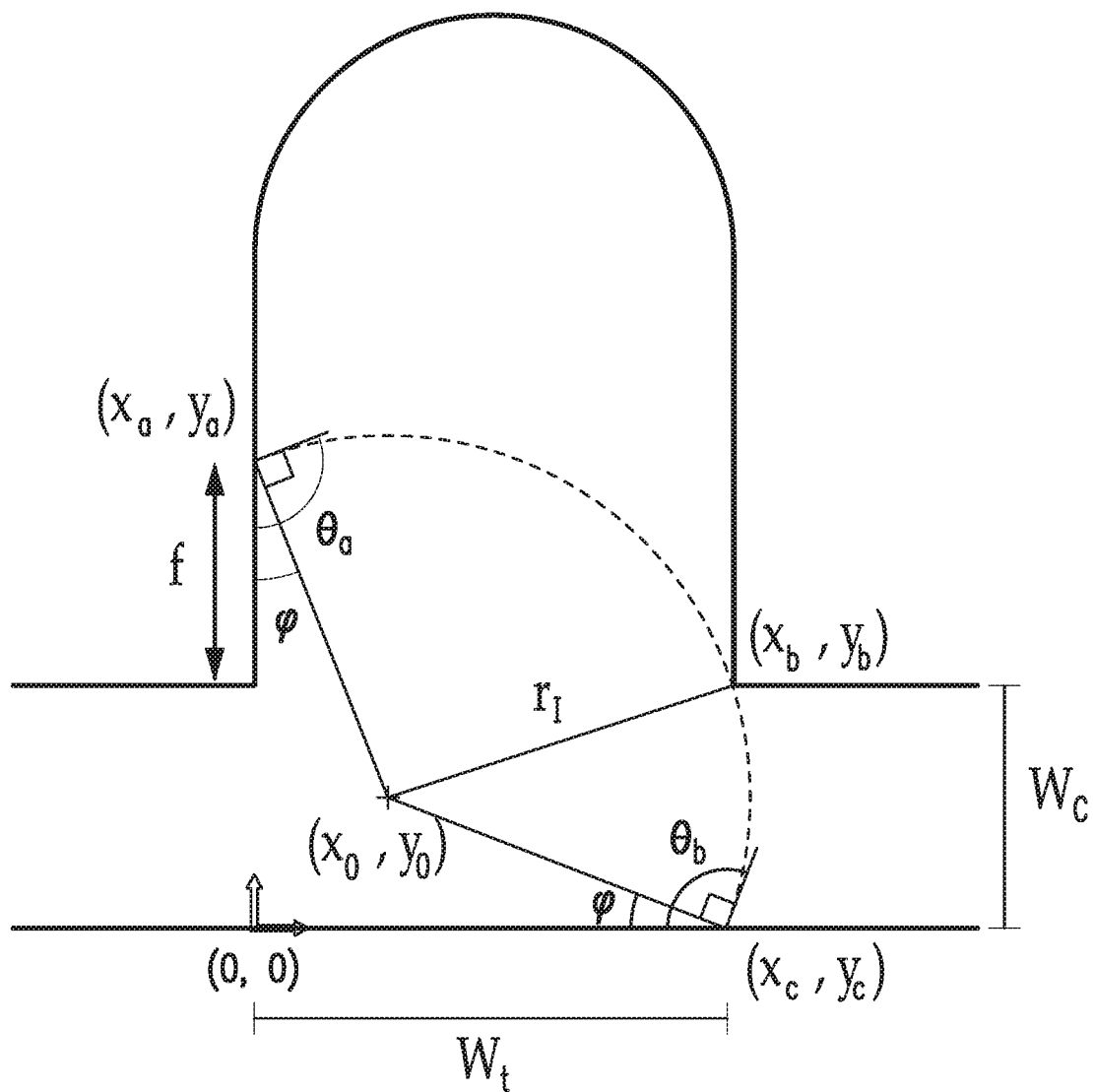
FIG. 2F is a geometric model for a single sided trap design.

The present invention is directed to sample digitization that supports passive self-discretization without the need for any external flow control or actuation. The technique exploits controlled pinning of fluid at geometric discontinuities within a microchannel, and may be applied to devices manufactured from any material with defined surface properties, including thermoplastics. Specifically, the present technique enables digitization of an aqueous sample in a thermoplastic cyclic olefin polymer (COP) microfluidic device, taking advantage of the polymer's moderate surface energy to achieve fully passive self-discretization without the need for any external pumps or other flow control elements.

Furthermore, an analytic model was used for predicting the maximum ratio of trap depth to trap width at which complete trap filling will occur. The model was validated through an experimental evaluation of the filling process using a set of devices fabricated with parametrically-varying trap geometries. Finally, the model was used as a predictive tool for the design and fabrication of a high aspect ratio staggered trap array, allowing the reliability of the filling process to be evaluated in a high density format.

FIG. 1A is an illustration of workflow in a self-loading and digitizing (SLD) device 100 comprising an inlet port 116, a main microfluidic channel 102, sample traps 104, a capillary pump 106, and an outlet port 112. The sample traps 104 are lateral protrusions emerging from the sides of the main microfluidic channel 102. A sample solution 110 is received at the inlet port 116 to flow along the main channel 102 filling the sample traps 104. In one embodiment, the sample solution 110 is delivered to the inlet port 116 by a pipette 108. To purge excess sample from the main channel 102, the main channel 102 terminates into a large chamber 118 ending with the outlet port 112. The chamber 118 has integrated capillary pump 106 so that the main channel 102 can be backfilled with an immiscible phase for reducing sample evaporation, as well as encapsulating each digitized sample volume with an immiscible barrier to prevent unwanted sample contamination. In one embodiment, the capillary pump is in the form of an absorbent membrane. By way of example and without limitation, the absorbent membrane may be fabricated from hydrophilically modified polyvinylidene fluoride (PVDF). The sample traps 104 reside on the side of the main channel 102 to provide the greatest flexibility in designing of the trap geometry. In one embodiment, the SLD device 100 is constructed with thermoplastic polymer and loaded with an aqueous test solution with surfactant. By way of example and without limitation, the thermoplastic polymer may be cyclic olefin polymer (COP), a weakly hydrophobic polymer.

As further demonstrated in FIG. 1A, the sample 110 is received at the inlet port 116, step 122. Next, the sample 110 advances along the main channel 102 filling the traps 104, step 124. In step 126, an excess sample is absorbed by the capillary pump 106 leaving the main channel 102 empty (step 128). Next, in step 130, the main channel 102 is loaded with an immiscible phase 120 to fully isolate each sample trap 104. In one embodiment, the immiscible phase 120 may be oil.

The angle of the advancing sample front θa (FIGS. 2F, 3F, and 4F) is an important factor in the loading physics of the SLD device 100 and is a function of the surface interactions between the sample solution and substrate, as well as the effect of gravity on the fluid head in the inlet. In one embodiment, to achieve self-loading, a small amount of surfactant (by way of example and without limitation 0.06% w/w) was added to the sample solution. Each trap 104 is characterized by a trap aspect ratio (TAR) and fluidic aspect ratio (FAR) defined with reference to FIGS. 2B, 3B, and 4B. Specifically, TAR=$f_y/w_t$ and FAR=$w_c/w_t$, where $w_c$ is the main channel width, $w_t$ is the trap width, and $f_y$ is a distance the sample traveled into the trap.

For example, if the sample traps 104 were intended to be pre-spotted with assay reagents and digitized volumes were expected to remain discrete, the TAR could be designed such that the depth of the trap is greater than it takes for reagents to diffuse into the main sample flow during loading, which would cause contamination of downstream traps. Furthermore, the TAR determines the percentage of volume retained for analysis versus the amount of sample required to prime the device.

As demonstrated in FIG. 1A, approximately the volume of the main channel is lost because it is required to drive the sample front to the capillary pump (PVDF membrane) 106. The sample excess is wicked away leaving the main channel 102 for the immiscible phase (oil) 120 backfill. Moreover, due to the physics of loading via surface tension the ratio of trap height ($d_t$) to main channel height ($d_c$) cannot exceed 1 because in that case the advancing front would favor bypassing the trap due to the interfacial expansion required for it to enter. The trap height ($d_t$) and the main channel height ($d_c$) refer to the out-of-plane dimension for the main channel 102 and traps 104.

Finally, trap configuration with respect to one another is an important factor in a surface tension driven system as it contributes the front conformation during trap loading which ultimately contributes to the types of trap geometries and more specifically the trap aspect ratios that can be loaded effectively.

The spatial positioning of the sample traps 104 can be broken down in three distinct configurations: traps all along one side of the main channel 102 (single sided (SS)) as shown in FIG. 1B; traps on both sides of the main channel 102 directly adjacent (double sided (DS)) as shown in FIG. 1C; traps that are on both sides of the main channel 102, but centerline offset from one another (staggered (S)) as shown in FIG. 1D. FIG. 1A demonstrates the traps 104 in the staggered configuration.

In one embodiment, the SLD devices according to FIG. 1A were fabricated by providing channel and microwell features in a plaque using a computer numerical controlled 3-axis CNC machine. By way of example and without limitation, the plaque may be a COP plaque. A hydrophilically modified polyvinylidene fluoride (PVDF) absorbent membrane was cut to specific size. The plaque was immersed in a solution of decahydronaphthalene in ethanol, rinsed with ethanol, and blown dry with $N_2$. The absorbent membrane was then manually aligned to a chamber in the plaque before a sealing layer was pressed to the substrate in a hot press to complete the bonding. In one embodiment, the sealing layer is a thin film. By way of example and without limitation, the thickness of the thin film may be about 200 μm.

FIG. 2A demonstrates images taken during sample loading process for an SLD device having a single sided trap configuration (FIG. 1B). The single sided configuration consists of the traps 104 branching off the same side of the main channel 102. The loading process for this configuration as shown in FIG. 2B starts when the sample flow reaches the entrance of the trap. The side of the sample front that faces the trap will be pinned due to the change in geometry while surface energy will drive the other side of the advancing front along the main channel wall. Once, the critical angle for advancement is reached at the pining point the front begins to spread into the trap. Surface tension will stabilize the interface so that angle of the advancing front (θa) is equal on both sides of the interface. The advancing front will eventually make contact with the wall on the opposite side of the trap. At this point the front can no longer fill the trap because it has trapped air ahead of it. The conformation of the front when it touches the opposite wall will determine the distance it traveled into trap ($f_y$). After the front touches the opposite trap wall surface tension will force it to regain its unpinned contact angle φ on both sides of the trap, and this is true for all configurations. The unpinned contact angle φ is a contact angle of water on the thermoplastic surface which is a property of the substrate material and can be measured for any given substrate.

FIGS. 2B and 2F demonstrate a geometric representation for the single sided configuration at the instant the front touches the opposite trap wall at varying θa. The geometric model presented in FIG. 2F illustrates the relationship that θa, and fluidic aspect ratio (FAR) will have on the final conformation of the interface when it touches the opposite wall in the single sided configuration. From the geometric model of FIG. 2F, an analytical solution is derived using a set of equations and constrains to solve for each point where the interface makes contact with the wall as a way to predict the maximum TAR parametrically. The calculations are performed under the assumption of constant interface curvature. Referring to FIG. 2F, $x_o$, $y_0$, $y_a$, and r are unknown; $x_a=0$, $x_b=w_t$, $x_c=y_a$, $y_b=w_c$, $y_c=0$, $\varphi$ and $\theta$ are known. Furthermore, $y_a \geq w_c$ and $r_f \geq 0$. Equations (1)-(4) describe the geometry as presented in FIG. 2F.

$$x_0^2 + (y_a - y_0)^2 = r_f^2 \quad (1)$$

$$(w_t - x_0)^2 + (w_c - y_0)^2 = r_f^2 \quad (2)$$

$$(y_a - x_0)^2 + y_0^2 = r_f^2 \quad (3)$$

$$\tan\varphi = \frac{x_o}{y_a - y_0}; \quad \varphi = \theta a - \pi/2 \quad (4)$$

Equations (1)-(4) are solved for $f_y=y_a-w_c$.

TAR($f_y/w_t$) dependence on $\theta a$ is plotted in FIG. 2C for an experimental SLD device with dimensions $w_t=390$ μm and $w_c=200$ μm. The $\theta a$ range is defined by a lower limit of 45° because below this point the interface will have negative curvature and thus is not able to be defined by the system of equations where radial curvature is assumed positive and equal at each point. In a physical sense $\theta a<45°$ indicates high wettability between the sample and the substrate, so loading of high aspect ratios is not a concern. The maximum achievable TAR with these parameters is 1:1 at a $\theta a=45°$. As $\theta a \to 180°$ the TAR asymptotically approaches 0 because $f_y \to w_c$.

TAR dependence on the FAR($w_c/w_t$) is plotted in FIG. 2D for an SLD device using a fixed $\theta a=90°$, representing experimental conditions. The FAR range explored had an upper limit of five because at these aspect ratios the sacrificed sample volume required to load the traps would significantly outweigh retained sample—sample efficiency of 3.8%. This plot shows the highest achievable TAR is 1:1 as FAR→0, which decays to 0 as FAR→∞. The optimal design for this configuration is to minimize the FAR and achieve a TAR close to 1:1 and a theoretical sample efficiency of 99.7%.

FIG. 3A demonstrates images taken during the loading process for a double sided SLD. The double sided configuration shows traps 104 branching off from both sides of the main channel 102. The loading process for this trap arrangement starts when the sample flow reaches the entrance of the trap. The interface is pinned at both sides of the bifurcation into the traps until $\theta a$ is reached at which point the front will begin spreading down the trap walls. It is possible that the interface will be asymmetric if $\theta a$ is reached at different times due to the traps not being perfectly aligned, or pinning points not being a perfect 90° corner. This asymmetry will cause instability in the interface that will result in different travel distances into each of the traps. Eventually the advancing front will make contact with the wall on the opposite side of the trap and halt trap filling because of the air pocket formed ahead of it. Similar to the single side model, the conformation of the front when it touches the opposite wall will determine the distance it traveled into trap.

Figure 3F:
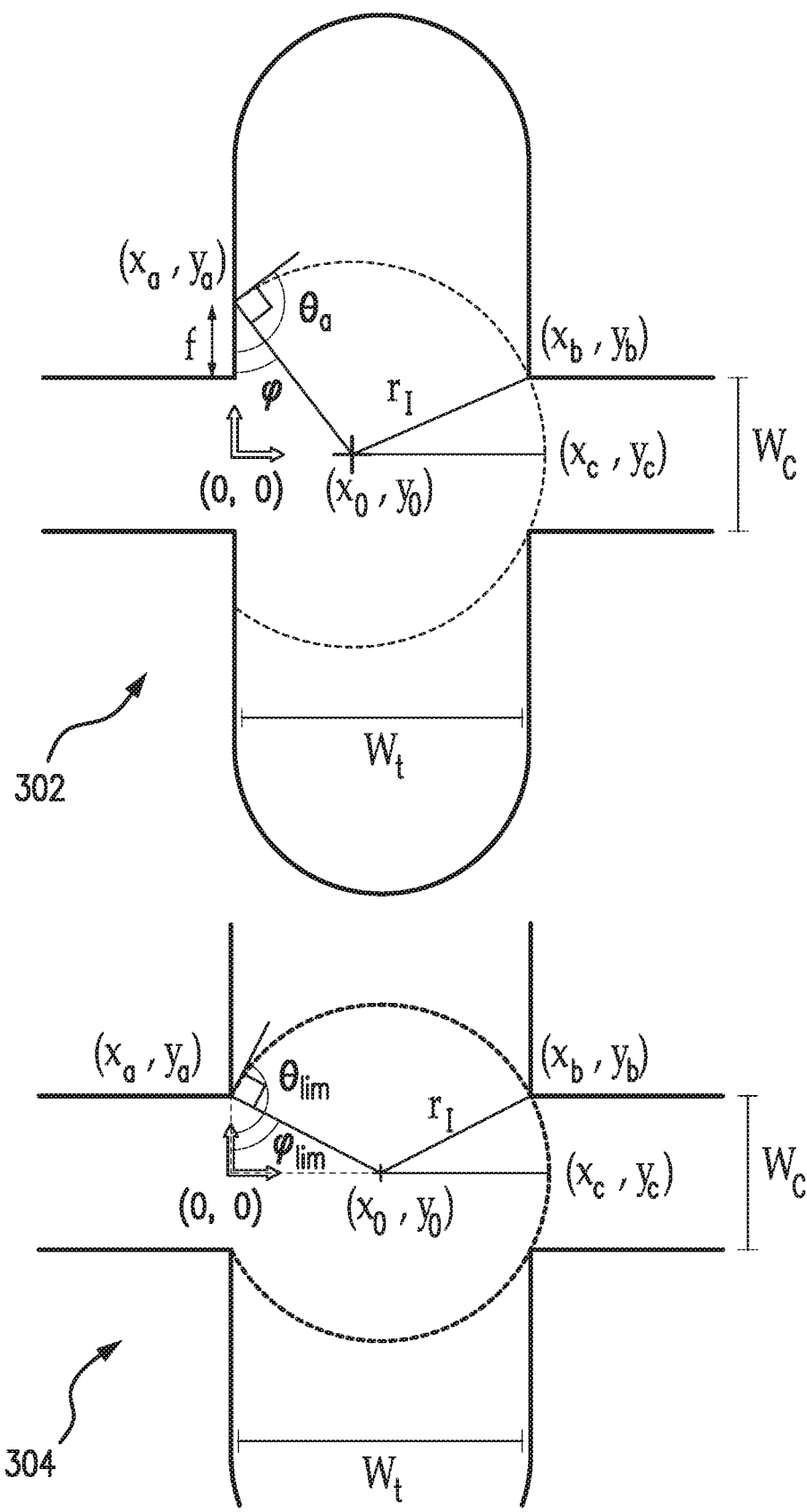
FIG. 3F is a geometric model for a double sided trap design.

The geometric model presented in FIGS. 3B and 3F illustrates the relationship that $\theta a$, and FAR will have on the final conformation of the interface when it touches the opposite wall in the double sided configuration. From this geometric model of FIG. 3F an analytical solution is derived using a set of specific equations and constrains to solve for each point where the interface makes contact with the wall as a way to predict the TAR parametrically. The calculations are performed under assumptions of constant interface curvature and symmetric advancement of interfaces along both trap walls. Referring to FIG. 3F, element 302, $x_o$, $y_0$ $y_a$, and r are unknown; $x_a=0$, $x_b=w_t$, $y_c=0$, $y_b=w_0/2$, $y_0=0$, $\varphi$ and $\theta$ are known. Furthermore, $y_a \geq w_c/2$, $r_f \geq 0$, and $\theta_{lim}$(FAR). Equations (1)-(3) describe the geometry as presented in FIG. 3F, element 302.

$$x_o^2 + y_a^2 = r_f^2 \quad (1)$$

$$(w_t - x_o)^2 + (w_c/2)^2 = r_f^2 \quad (2)$$

$$\tan\varphi = \frac{x_o}{y_a}; \quad \varphi = \theta a - \pi/2 \quad (3)$$

Equations (1)-(3) are solved for $f_y=y_a-w_c/2$. Referring to FIG. 3F, element 304, as the curvature is constant, $x_o=w_t/2$ and $y_a=w_c/2$;

$$\tan\varphi_{lim} = \frac{w_t}{w_c}$$

and $\theta_{lim}=\varphi_{lim}+\pi/2$.

TAR dependence on $\theta a$ is plotted in FIG. 3C for an SLD device with dimensions $w_t=390$ μm and $w_c=200$ μm to match experimental devices. Unlike the SS model, the $\theta a$ does not have a lower limit within the DS model but nevertheless is constrained to $\theta a>45°$ because of the wettability of the sample solution. The upper limit of $\theta a$ will be a function of the FAR and is derived in FIG. 3F. For the experimental device with wt=390 μm and we=200 μm the upper limit of $\theta a=152°$. At $\theta a=45°$ the TAR is approximately 2.2 and as $\theta a$ is increased the TAR decays 0 when $\theta a=152°$.

TAR dependence on the FAR is plotted in FIG. 2D for an experimental SLD device assuming a fixed $\theta a=90°$, representing experimental conditions. The FAR range explored had an upper limit of 5 because at these aspect ratios the sacrificed volume required to load sample would significantly outweigh retained volume—sample efficiency of 13.8%. This plot shows the highest achievable TAR is 1:1 as FAR→0, which decays to 0 as FAR→∞. The optimal design for this configuration is to minimize the FAR to achieve a TAR close to 1:1 and a theoretical sample efficiency of 99.9%.

FIG. 4A illustrates images taken during the loading process for a staggered SLD device. The staggered configuration shows the arrangement of traps 104 branching off from both sides of the main channel 102 but instead of being aligned directly opposite they are centerline offset.

The loading process for the staggered trap arrangement, as shown in FIG. 4A, starts when the sample flow reaches the entrance of the trap. The interface is pinned at the opening while the other side of the front is able to traverse the main channel. Flow will continue along the main channel wall until it gets pinned on the opposite side trap entrance. When the front is pinned on both sides the interface will expand and allow the critical angle for advancement to be reached at the first pinning point. The front will then begin to spread down the first trap wall and eventually make contact with the wall on the opposite side of the trap and halt trap filling because of the air pocket formed ahead of it. The conformation of the front when it touches the opposite wall will determine the distance it traveled into trap.

Figure 4F:
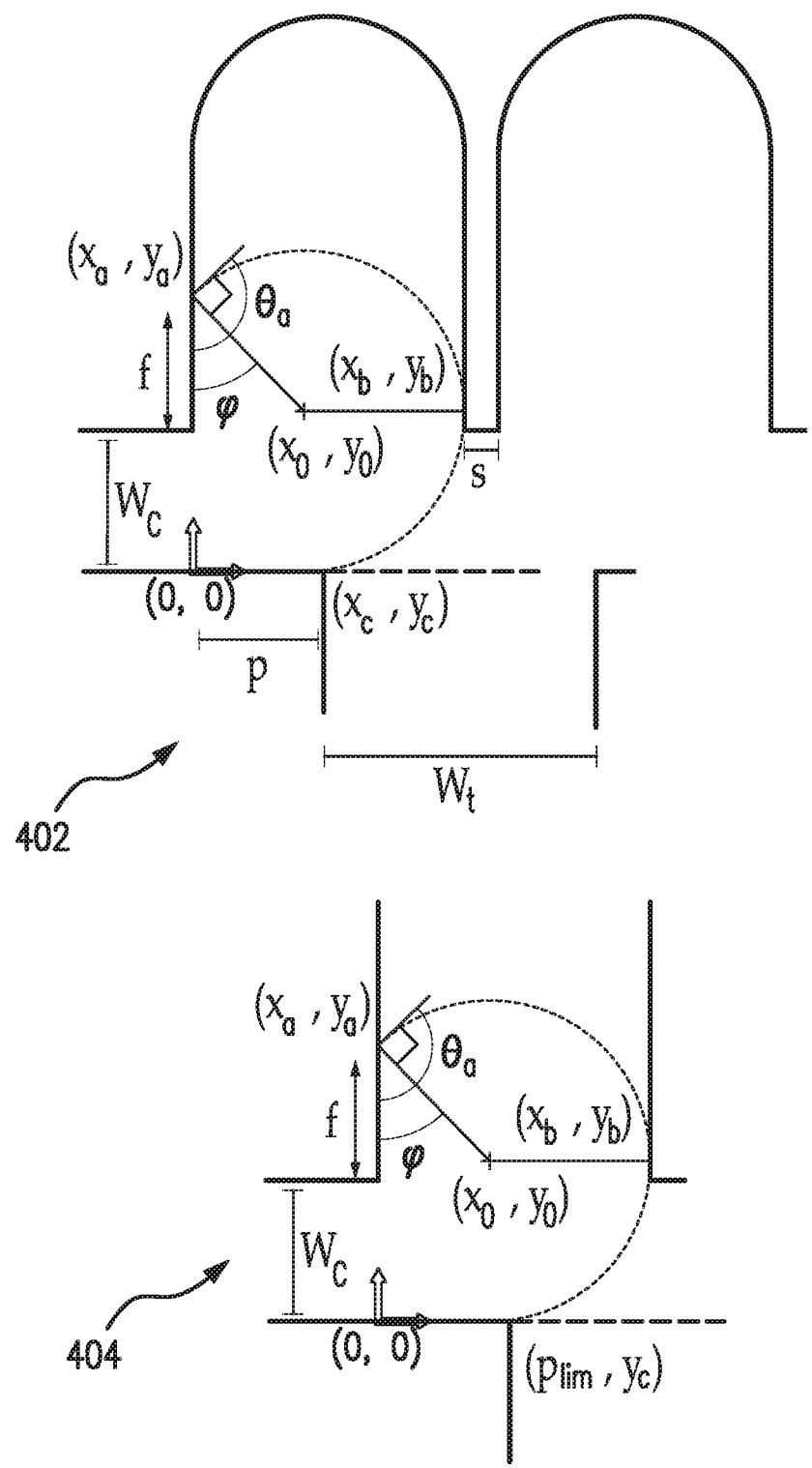
FIG. 4F is a geometric model for a staggered trap design.

The geometric model presented in FIGS. 4B and 4F illustrates the relationship that θa, FAR, and pinning offset ratio (POR) will have on the final conformation of the interface when it touches the opposite wall in the staggered configuration. The pinning offset (PO) is defined as the distance that separates the entrance to the opening of the trap to the pinning point established by the opening to the trap opposite of it. The POR is just the PO normalized to trap width ($w_t$). The PO is different on each side of the main channel because on the staggered side the pinning offset will include a barrier wall. So the pinning offset in the staggered row PO*=($w_t$−PO)+$w_b$. From the geometric model of FIG. 4F, element 402, an analytical solution is derived using a set of specific equations and constrains to solve for each point where the interface makes contact with the wall as a way to predict the TAR parametrically. The calculations are performed under the assumption of constant interface curvature. Referring to FIG. 4F, element 402, the calculations are made under the assumption of constant interface curvature. Variables $x_o$, $y_0$, $y_a$, and r are unknown; $x_a$=0, $x_b$=$w_t$, $x_c$=p, $y_b$=$y_0$, $y_c$=0, φ and θ are known. Furthermore, $y_a$≥$w_c$, $y_0$≥$w_c$, and $r_l$≥0. Equations (1)-(4) describe the geometry as presented in FIG. 4F, element 402.

$$x_o^2 + (y_a - y_0)^2 = r_l^2 \quad (1)$$

$$(w_t - x_o)^2 = r_l^2 \quad (2)$$

$$(p - x_o)^2 + y_0^2 = r_l^2 \quad (3)$$

$$\tan\varphi = \frac{x_o}{y_a - y_0}; \quad \varphi = \theta a - \pi/2 \quad (4)$$

Equations (1)-(4) are solved for $f_y$=$y_a$−$w_c$.

For FIG. 4F, element 404, calculations are made under the assumption of constant interface curvature. Variables $x_o$, $y_0$, $y_a$, and r are unknown; $x_a$=0, $x_b$=$w_t$, $y_a$=$p_{lim}$ ($p_{lim}$ is also referred to as pinning offset (PO)), $y_c$=0, φ and θ are known. Furthermore, $y_a$≥$w_c$, and $r_l$≥0. Equations (1)-(4) describe the geometry as presented in FIG. 4F, element 404.

$$x_o^2 + (p_{lim} - y_0)^2 = r_l^2 \quad (1)$$

$$(w_t - x_o)^2 + (w_c - y_o)^2 = r_l^2 \quad (2)$$

$$(p_{lim} - x_o)^2 + y_0^2 = r_l^2 \quad (3)$$

$$\tan\varphi = \frac{x_o}{p_{lim} - y_0} \quad (4)$$

Equations (1)-(4) are solved for $p_{lim}$(TAR, θa) using the single sided model. If p>$p_{lim}$, then pinning does not occur for that configuration.

TAR dependence on θa is plotted in FIG. 4C for an experimental SLD device with dimensions wt=390 μm and wc=200 μm and POR=0.55. Similar to the DS model, the θa does not have a lower limit but is constrained to θa>45° because of the wettability of the sample solution. At θa=45° the TAR is approximately 3.7 for test device, and as θa is increased the TAR decays to 0 when θa=180°.

TAR dependence on the FAR is plotted in FIG. 4D for an experimental SLD device using a fixed θa=90° with varying PORs. The FAR range explored had an upper limit of 1 because of the model . . . . This plot shows the highest achievable TAR of 2:1 as FAR→0 which decays linearly to 1 as the FAR→1. The optimal design for this configuration is to minimize the FAR and the POR to achieve a TAR close to 2:1 and a theoretical sample efficiency of 99.9%.

FIG. 4D also plots single sided (SS) and double sided (DS) models for comparison. The TAR DS and TAR SS will have the same limit of 1 as FAR→0, while the TAR DS decays to 0 at a lesser rate than TAR SS as the FAR→∞. As the POR approaches a limit, a function of the FAR (See FIG. 4F), the TAR S dependence acts as if it were a single sided configuration. This can be explained physically because at sufficiently high POR the front will touch the opposite trap wall before it can reach the pinning point and succumb to its affects. Overall, the staggered model predicts a drastic improvement over both the double sided and single sided configurations for filling aspect ratios greater than 1. Furthermore, the staggered configuration enables control over diffusion lengths of pre-deposited reagents within traps mitigating risk of cross contamination, a necessity for certain applications.

Prior reported digitization platforms commonly initialize operations with an oil phase plus surfactant which inhibits sample/substrate interaction making digitization effectiveness highly dependent on the control over pressure driven flow. On the other hand, by eliminating the oil initialization step and instead harnessing the surface energy of the substrate, it is not only possible to eliminate unnecessary workflow but also leverage surface energy to improve digitization effectiveness.

Figure 5:
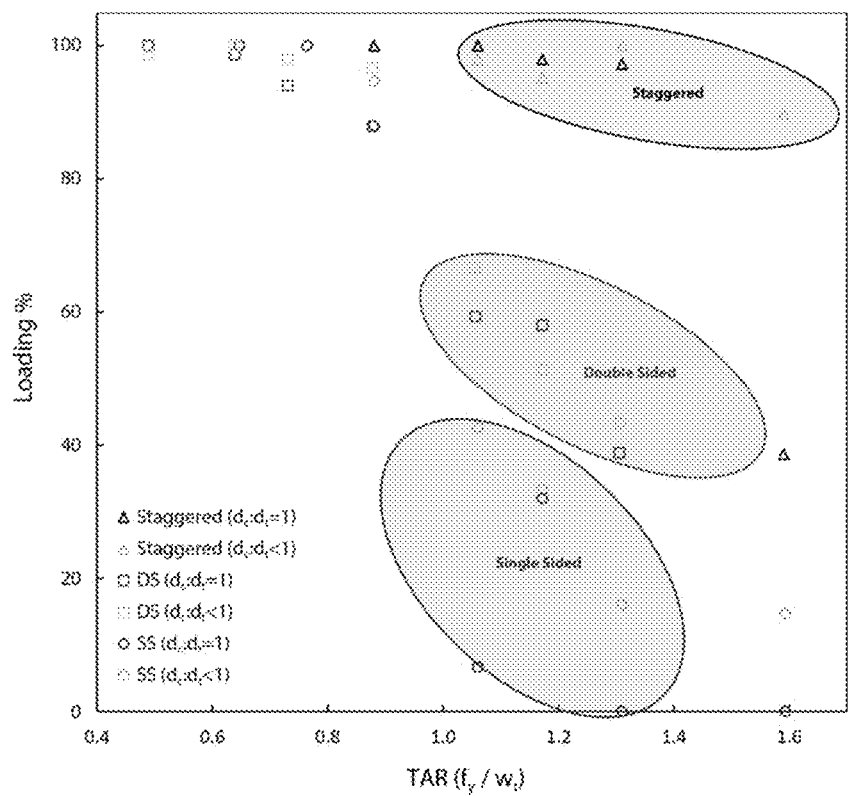
FIG. 5 illustrates the sample loading percentage for different trap configurations at different aspect ratios. Two data sets (light and dark) for each trap configuration represent a difference in heights between the main channel and the trap.

FIG. 5 illustrates loading percentage (%) of the different trap configurations at different aspect ratios. Two data sets (light and dark) for each trap configuration represent a difference in heights between the main channel and the trap. There are several important considerations such as interfacial instability caused by alignment asymmetry, non-sharp pinning points, and surface roughness that may cause a deviation from the model in experimental SLD devices. In practice, these effects result in a gradient in terms of loading percentage decay around the predicted TAR limit as opposed to a sharp drop off. Another important distinction is that the traps have curvature at the top which changes the interface dynamics when it traverses the curvature in such a way that it is difficult to incorporate into the model. It is not sufficient to just assume filling will be spontaneous once it gets to the curved portion because at the limit the interface will be unstable and also will be very close to the opposite wall. To address this, the TAR, as defined in the experimental devices, includes the curvature at the top as opposed to where the curvature starts because filling is assumed to be spontaneous after that point. This will push the loading percentage limit to above the theoretical limit predicted by the model to account for the improved but not absolute filling in the curved section.

In one embodiment, 35 different SLD devices at varying trap aspect ratios, main channel height ($d_c$) to trap height ($d_t$) ratios, and trap configurations were fabricated for testing. For each loading trial a test solution of DI water, glycerol, blue food coloring (for imaging) and a small concentration of TritonX100 surfactant (0.06% w/w) was used. The surfactant was added to aid self-filling. The measured advancing contact angle of the sample solution was 90°.

In yet another embodiment, each of the 35 SLD chips had a $w_c$=200 μm and $w_t$=390 μm because those are the smallest dimensions that could be repeatedly produced at a high quality with computer numerical control (CNC) machining. Additionally, the ratio of the main channel height to the trap height was varied to explore the effects of improved capillarity in the traps during loading. The total amount of traps on each chip was 15 for SS, 30 for DS, and 29 for S configurations so that all traps could be visible within the field of view of the microscope. Each chip was loaded with 2 µL of test solution and then subsequently examined under microscope to determine the amount of traps successfully loaded. The SLD traps ability to load sample solution into them without trapping air, or its loading percentage, was the performance metric that each design was evaluated by. More specifically, the fraction of traps that were completely filled with sample over the total number of traps in the device was recorded for 5 trials per device with the loading percentage being the mean of those 5 trials. The trapping of air bubbles is of particular concern for digitization applications where polymerase chain reaction (PCR) is employed because adverse effects of thermal expansion in a closed microfluidic system. Furthermore, incomplete filling makes it unsuitable for applications where uniform aliquots are needed for proper quantification, such as in digital qPCR. The loading percentage results as demonstrated in FIG. 5 show as predicted by the numeric model that there is a significant difference in trap loading percentage for each configuration as the TAR exceeds 1. The staggered configuration maintains a high loading percentage at TARs>1, showing that even with non-ideal conditions the pining effect is significant.

FIGS. 6A-6C illustrate the design space for the single sided, double sided, and the staggered configurations, respectively. The geometric model trap aspect ratio threshold is denoted by a black dashed line with the area shaded in green representing the parametric combinations the model predicts will have a high loading percentage. Data points for each parametric combination are plotted and connected by a solid black line and its shadow is color coded for each FAR/POR. The data points that lie beyond the model threshold are shaded with a darker color and correspondingly show a sharp drop-off in loading percentage while the more transparent shadow represents data that falls in the region of expected high loading percentage.

In one embodiment, 46 different SLDs chips (15 S, 15 SS, and 16 DS) were tested to assess loading percentage parametrically. SLD devices with FARs of 0.01, 0.26, 0.51, and 1.00 for DS and SS configurations, and a FAR of 0.55 with POR of 0.01, 0.13, 0.26, 0.51, and 1.00 for the staggered configuration were fabricated and tested using the same loading protocol. FIGS. 6A-6C show the design space for the single sided (FIG. 6A), double sided (FIG. 6B), and staggered (FIG. 6C) configurations. Each model shows a gradient in loading percentage decay in the vicinity of the limit. It also maintains that despite non-ideal conditions the staggered design will have significantly better loading percentage at TAR>1 which decays as the POR increases.

FIG. 7A is an image taken of an SLD chip array 700 after loading operations. In one embodiment, the SLD chip array 700 has 768 traps 104 loaded with sample and backfilled with oil to isolate the trapes 104. To demonstrate the scalability of the SLD chip, a 768 trap array was fabricated with 6 parallel channels, each comprising of 128 traps 104. The robust filling mechanism of the SLD chip provides it with the flexibility to design any combination of parallel main channels with any number of in series traps depending on the specific assay/application and time constraints.

In one exemplary embodiment, traps 104 in the array were designed to have a trap aspect ratio of 1.1 and held approximately 11 nL of sample when completely filled. To load the device, 2.1 µL sample solution was introduced into each parallel channel which loaded 128 traps plus a sacrificial 129th trap in approximately 1.5 min. The 129th trap served as a sacrificial trap so that the 128th trap would have a pining point. During loading 765 out of 768 traps were loaded (99.6%) without trapping air following closely to the aforementioned model for the device design. In total, 12.6 µL of sample solution was used to load the whole device in approximately 5 min with an estimated sample retention of 60%.

FIG. 7B shows a histogram of the trapped volumes in the SLD array. A MATLAB image analysis script was used on a composite image of the array for acquiring area measurements or each trap based on a pixel count. A standard deviation of 1.36 (nL) in volume captured for each trap was measured.

Figure 7C:
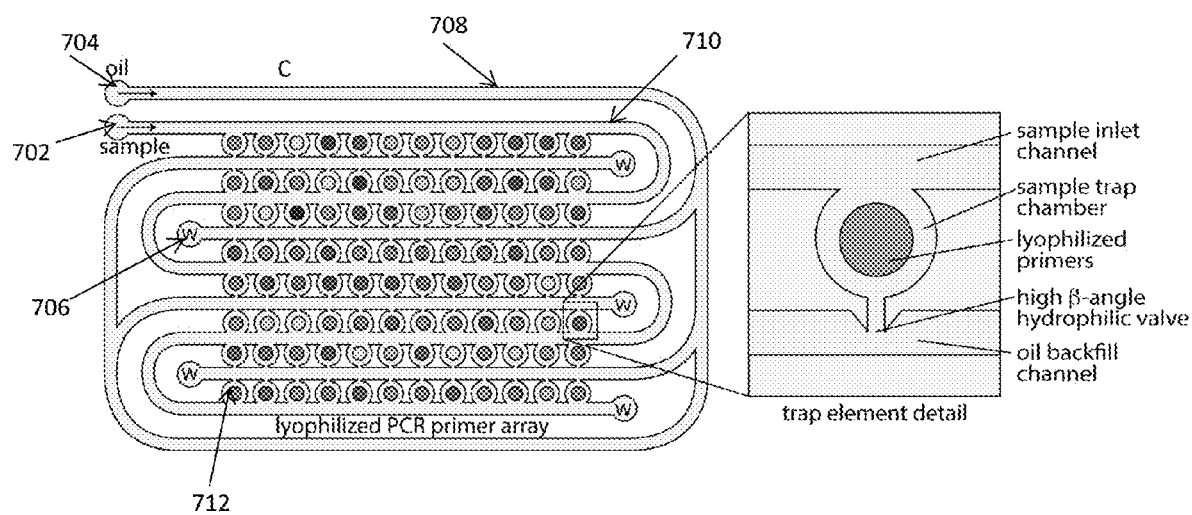
FIG. 7C illustrates an SLD chip having a trap array according to another embodiment of the present invention.

FIG. 7C illustrates a self-loading chip according to another embodiment of the present invention. The self-loading chip comprises a sample inlet port 702, an oil inlet port 704, an outlet port 706, a sample inlet channel 710, an oil backfill channel 708, and sample traps 712. The sample traps 712 are in fluid communication with both the sample inlet channel 710 and the oil backfill channel 708. Each trap is connected to the oil backfill channel 708 through a high β-angle hydrophobic valve to prevent sample from leaking from the trap chamber 712 into the backfill channel 708 during sample filling. Furthermore, each trap 712 comprises lyophilized reagents. In one embodiment, the lyophilized reagents include primers for performing a nucleic acid amplification reaction. The pre-deposited reagents may be loop-mediated isothermal amplification (LAMP) reagents, Polymerase Chain Reaction (PCR) reagents, Nucleic acid sequence based amplification (NASBA) reagents, Helicase-dependent Amplification (HAD) reagents, Strand Displacement Amplification (SDA) reagents, Recombinase polymerase amplification (RPA) reagents, Hybridization Chain Reaction (HCR) reagents, or Rolling Circle Amplification (RCA) reagents including primers to amplify target nucleic acids in the sample.

Exemplary Embodiment 1. Chip Fabrication

Figure 8A:
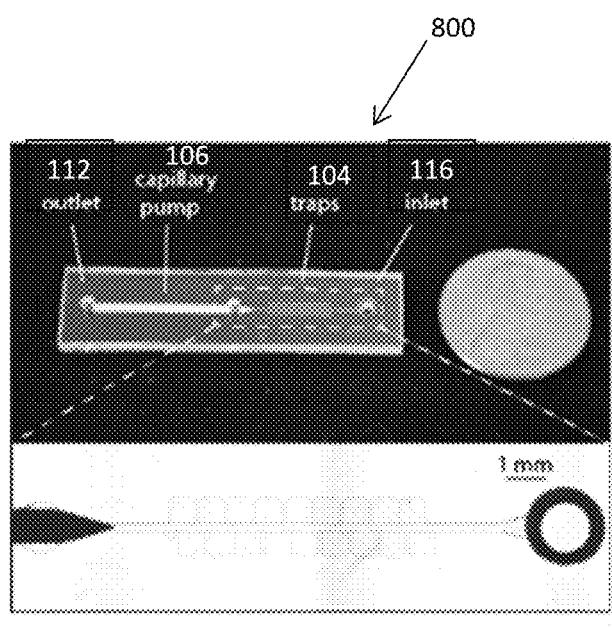
FIG. 8A illustrates an image and schematic for an SLD chip according to one embodiment of the present invention.
Figure 8B:
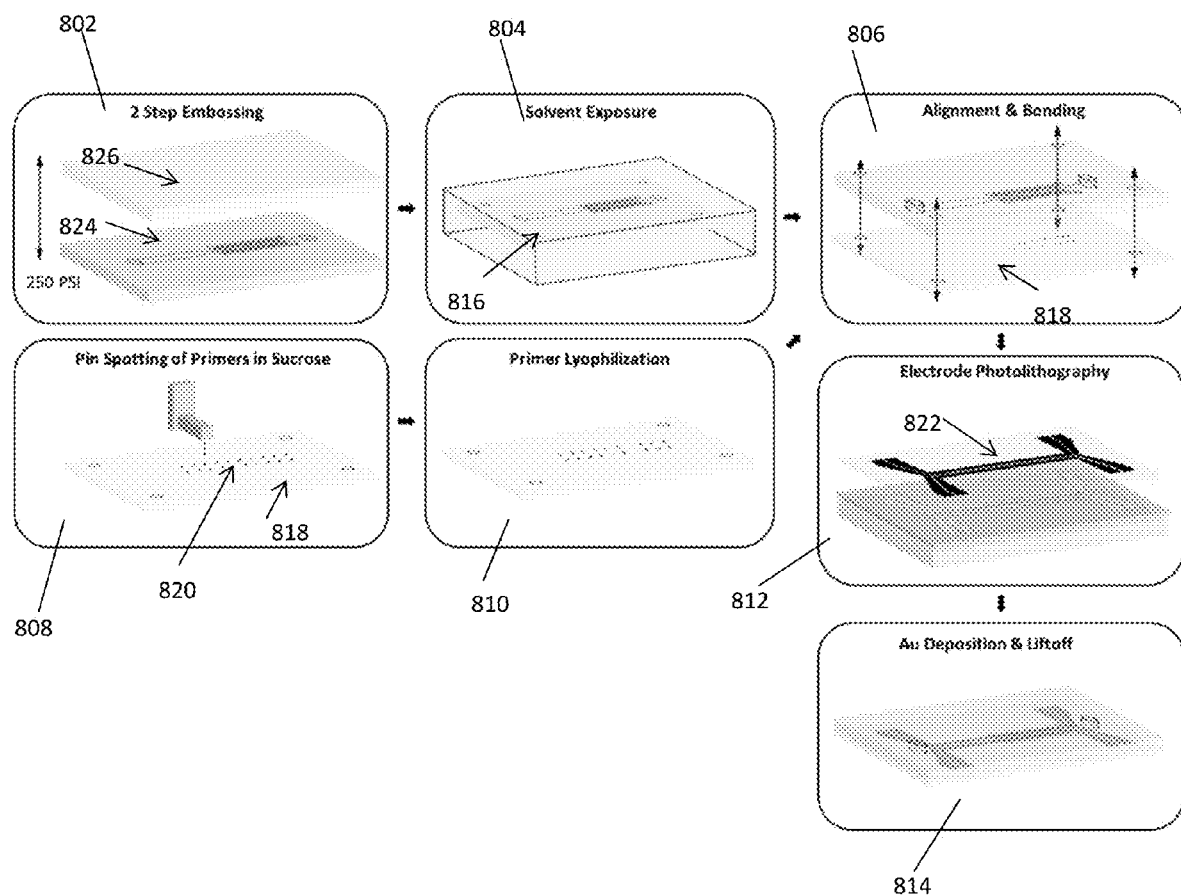
FIG. 8B is a flowchart illustrating fabrication process of an SLD chip as shown in FIG. 8A.

In one aspect of the present invention as shown in FIG. 8B, a self-loading and digitizing (SLD) device such as the chip 800 demonstrated in FIG. 8A was fabricated from a thermoplastic. In one embodiment, COP was used due to its high transparency, low autofluorescence, low water absorption, and low gas permeability, making it a suitable substrate material for PCR. The microfluidic features can be created by any number of ways including single-step embossing (if all features are the same height), two-step embossing (for different heights), milling, as well as injection molding and other common techniques for thermoplastic patterning.

Specifically, in the embodiment of FIG. 8B, a channel layer 824 was fabricated from a thermoplastic substrate in a two-step embossing process (step 802). In one embodiment, a mold 824 was fabricated using CNC machining to create a plurality microfluidic features including a microfluidic channel 102, sample traps 104, inlet/outlet ports 112/116, and a capillary pump chamber 106. Then, a thermoplastic substrate 826 was pressed against the mold 824. In step 804, the substrate is solvent exposed. Parallel with the substrate fabrication of steps 802 and 804, reagents 820 are pin spotted on a sealing layer 818 in step 808. In one embodiment, the regents include primers in sucrose. Then, the reagents were lyophilized in step 810. The channel layer 826 was also milled with alignment holes 816 in each corner so that it could be aligned to protruding pins on the pin spotting stage 818 that would keep it aligned with the same origin on the pin spotter each time (step 806).

In one embodiment, two PVDF membranes were patterned using a craft cutter and were then inserted into a pre-milled chamber 106 on the channel layer 826. A pointed shape at the front of membrane provided the best performance in terms of purging excess sample from the main channel. The milled substrate was then mated to the thin film COP with deposited reagents 820 face down on the spotting stage 818. Tape on the COP film was wrapped around the substrate on top to hold it together until the appropriate pressure applied was used to complete bonding in step 806. Electrode photolithography was performed in step 812, followed by Au deposition and liftoff in step 814.

In one exemplary embodiment, the channel layer of the SLD chip as shown in FIG. 8A was fabricated by milling channel and microwell features in a 2 mm thick COP plaque (by way of example and without limitation, Zeonor 1020, Zeon Chemicals, Louisville, Ky.) to a depth of 250 μm using a 3-axis CNC machine (by way of example and without limitation, MDX-650, Roland DGA, Irvine, Calif.). A 125 μm thick hydrophilically modified polyvinylidene fluoride (PVDF) membrane with 5 μm pore size (by way of example and without limitation, SVLP04700, EMD Millipore, New Bedford, Mass.) was patterned using an automated craft cutter (by way of example and without limitation, Cameo Digital Craft Cutting Tool, Silhouette America, Orem, Utah). The capping layer of the SLD chip was patterned from a 50 μm thick cyclic olefin copolymer (COC) film (by way of example and without limitation, Zeonex 1420, Zeon Chemicals). The COC film was affixed to the pin spotting stage with tape to prevent movement. Primer solution consisting of 20% (w/w) polyethylene glycol (PEG) was loaded into the pin using capillary action and then deposited when the pin made contact with the film. After deposition the PEG/primer spots were left to completely dry at 45° C. for 15 min before a protective layer of soft paraffin wax (by way of example and without limitation, Vaseline, Unilever, USA) was deposited at a temperature 42° C. over top of the dried PEG spots. The microchannel substrate was next exposed to 35% (w/w) decalin (by way of example and without limitation, ThermoFisher Scientific, Rockford, Ill.) in ethanol for 1.5 min, rinsed with 100% ethanol, and blown dry with $N_2$. Two identically patterned PVDF membranes were stacked for a total thickness of 250 μm and inserted into a mating chamber in the COP substrate. The decalin-solvated channel substrate and capping layer were then aligned using pins built into an alignment stage and mated to seal the channels and microwells. The chip assembly was then placed in a hot press (by way of example and without limitation, AutoFour/15, Carver Inc., Wabash, Ind.) at 200 psi and 23° C. for 10 min to complete the bonding.

In yet another exemplary embodiment, a custom pin spotting tool was provided for the controlled deposition of PCR reagents onto COP films. The tool consisted of three linear actuators (by way of example and without limitation, MX45S, Parker Hannifin Corp., Cleveland, Ohio) attached to stepper motors (by way of example and without limitation, LV141-02-10, Parker Hannifin Corp., Cleveland, Ohio) for X, Y, and Z axis control. Photoelectric sensors with 30 μm repeatability (by way of example and without limitation, PMY44P, Parker Hannifin Corp., Cleveland, Ohio) were used to calibrate the origin and provide limit stops to protect the actuators from damage. The motors were driven by a motor driver (by way of example and without limitation, ED-Drive, Parker Hannifin Corp., Cleveland, Ohio) enabling positioning resolution of 1 μm, and controlled using an Arduino Uno microcontroller (by way of example and without limitation, Adafruit, New York, N.Y.) and GRBL open source software for the graphical interface. The Z-axis actuator controlled the height of various sized pins (by way of example and without limitation, Xtend Microarray Pin, LabNext, Inc., West New York, N.J.) that deposited nanoliter scale volumes through contact printing. The spotting stage was equipped with mechanical alignment pins for gross positioning of the channel layer to the spotter. The stage was also equipped with two Peltier heaters; one positioned under the spotting film, and one in a peripheral location to heat the wax bath.

Exemplary Embodiment 2. Chip Fabrication

The SLD devices according to FIG. 1A and FIG. 7A were fabricated by milling channel and microwell features in a COP plaque (by way of example and without limitation, a 2 mm thick plaque, Zeonor 1020, Zeon Chemicals, Louisville, Ky.) using a computer numerical controlled 3-axis CNC machine (by way of example and without limitation MDX-650, Roland DGA, Irvine, Calif.). A hydrophilically modified polyvinylidene fluoride (PVDF) absorbent membrane (by way of example and without limitation, SVL04700, EMD Millipore, New Bedford, Mass.) was cut to specific size using an automated craft cutter (by way of example and without limitation, Cameo Digital Craft Cutting Tool, Silhouette America, Orem, Utah). The milled COP plaque was immersed in a solution of 35% decahydronaphthalene (by way of example and without limitation, Thermo Fisher Scientific, Rockford, Ill.) in ethanol (w/w) for 1.5 min, rinsed with ethanol, and blown dry with $N_2$. The absorbent membrane was then manually aligned to a premilled chamber in the COP plaque before the multilayer device was pressed at 200 psi and 23° C. for 10 min in a hot press (by way of example and without limitation, AutoFour/15, Carver Inc., Wabash, Ind.) to complete the bonding.

Exemplary Embodiment 3. Self-Loading and Digitization Operation

Loading experiments for all SLD devices according to the present invention were conducted by using a pipette to manually load 2 μL of DI water containing 0.06% (w/w) TritonX100 (Sigma Aldrich), glycerol, and blue food coloring. Once the sample primed the device and the absorbent membrane removed excess sample, the chip was imaged under the microscope (by way of example and without limitation, AZ100, Nikon Instruments Lewisville, Tex.) to identify the number of traps that had been successfully loaded. The trapping of small air bubbles or incomplete loading of a well would be considered unsuccessful. Priming and purging was accomplished in approximately 30 s for devices with 30 or fewer traps, while the higher density device was primed and purged within approximately 5 min.

An SLD devise according to one embodiment of the present invention is provided to perform highly scalable multiplexed PCR with minimal manual input. Specifically, FIG. 8A illustrates a thermoplastic self-loading chip 800 comprising an inlet port 116, an outlet port 112, a capillary pump 106, a microchannel 102. The microchannel 102 connects the inlet port 116 to the capillary pump 806 at the outlet 112 with staggered wells (traps) 104 in between. The array of microwells 104 serves to isolate discrete sample volumes, while PCR reagents integrated into the chip during fabrication allow for different reactions to be performed within each discretized volume.

Reagents are integrated into the wells by pin spotting sequence-specific PCR primers in a paraffin wax matrix, ensuring that the primers remain encapsulated during sample introduction while enabling temperature-controlled release prior to thermocycling. In one embodiment, the reagents are lyophilized. In yet another embodiment, reagents may be deposited by piezoelectric inkjet, screen printing, and solid-phase deposition.

The sample itself is manually deposited by pipette into the inlet port 116, with passive filling and discretization of the entire microwell array achieved by capillary pumping as shown in FIG. 1A. Effective self-filling of the thermoplastic reaction chambers is achieved through the use of a staggered array design that employs geometric fluid pinning to promote highly repeatable filling of the high aspect ratio microwells (traps). In one embodiment, the capillary pump 106 is a PVDF membrane.

In one exemplary embodiment, microwell dimensions of 900 μm square and 250 μm deep were chosen to accommodate the paraffin wax covered reagents and provide sufficient reaction volume for effective PCR from dilute samples while still providing reliable self-filling and digitization.

In one embodiment, chip loading was performed by pipetting sample solution in the inlet 116 of the chip 800. Excess sample was removed by the integrated PVDF membrane 106 downstream and then an immiscible phase was loaded into the chip 800 to fully isolate each reaction well (trap). Once loaded, a single piece of PCR-compatible adhesive tape was used to seal the top side of the chip. The chip was then placed on a thermocycler comprising a Peltier element controlled by a microcontroller. The software-defined PCR routine implemented by the microcontroller was performed. The microcontroller actuated a LED light source (not shown) and a CCD camera (not shown) placed directly above the chip to collect fluorescence output during the extension step of the PCR reaction.

In one exemplary embodiment, 3.75 μL of sample solution was pipetted into the inlet port 116 of the chip 800. Excess sample was removed by the integrated PVDF membrane 806 downstream and then 5 μL silicone oil (for example, AR20, Sigma-Aldrich, St. Louis, Mo.) was loaded. The PCR reaction consisted of a 120 s hot start at 95° C., followed by 20 cycles of 95° C. for 15 s, 60° C. and 72° C. for 30 s. The microcontroller actuated the 452 nm LED light source and a CCD camera collected fluorescence output during the extension step (72° C.).

Preventing the rehydration of integrated primers during sample introduction is essential to the proper functioning of the SLD chip. Without slowing rehydration, primers will be carried by the fluid front and transported downstream cross contaminating subsequent sample traps.

In one embodiment, polysaccharides were selected for a dissolution retarding matrix for the integrated primers. Specifically, sucrose, dextran, and polyethylene glycol (PEG) were selected for their solubility in water, and general biocompatibility with polymerase chain reaction. Each was dissolved at concentrations ranging 10% to 40% (w/w) and mixed with fluorescein salt. Specifically, in one exemplary embodiment, a concentration of 20% (w/w) for each polymer was found to successfully balance viscosity appropriate for deposition and dissolution time. The different mixtures were spotted on the COP substrate and dried down. A droplet of water with a comparatively large volume was added to the spot and fluorescence was recorded over time. In this way the approximate dissolution time (diffusion limited) for each additive was determined.

Figure 9:
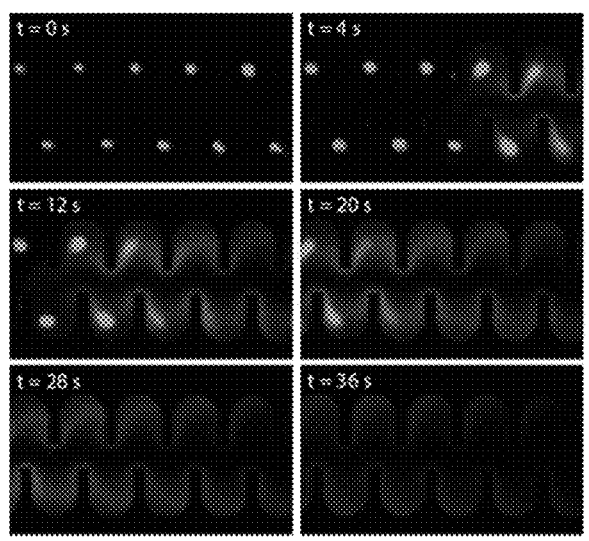
FIG. 9 illustrates an image sequence of PEG and fluorescein salt being rehydrated by sample self-loading in the SLD chip of FIG. 8A.

Accordingly, sucrose, dextran, and PEG spots were incorporated into an SLD device. Then, a sample solution was self-loaded to confirm the effect of advective flow in the sample traps. Fluorescence in the traps was recorded over time to determine the approximate dissolution time with the addition of advection. FIG. 9 shows fluorescence images over time from PEG 20% (w/w) and fluorescein salt spots as sample solution is self-loading through the chip as shown in FIG. 8A.

In yet another embodiment, gelatin was tested to retain primers to the trap during sample loading. Gelatin improved diffusion limited transport and could fully expel the incorporated dye when heated above its melting point, however during device testing once the gel was hydrated advection would dominate dissolution and disperse the fluorescein salt at a similar time scale to sucrose and PEG.

In one embodiment, to mitigate the effects of advection, paraffin wax, a hydrophobic material containing hydrocarbons of the general formula $C_nH_{2n+2}$, was used. Paraffin wax has been shown to be both compatible with PCR and able to protect dried reagents against flow. A robust coating of paraffin overtop of a primer spot provides an indefinite protective barrier to primer dissolution. The paraffin could be heated to above its melting point after sample solution was loaded to disperse the primers into corresponding sample traps (reaction chamber). Table 1 summarizes the spotting and dissolution data for the mentioned additives.

TABLE 1

Summary of primer additive materials for reagent integration

| MATERIAL | SPOTTING VARIABILITY | CONTROLLED RELEASE | DISSOLUTION TIME (DIFFUSION) | DISSOLUTION TIME (DIFFUSION + ADVECTION) |
| --- | --- | --- | --- | --- |
| Sucrose (20%) (MW = 310 Da) | σ = 5.9% | No | 20 s | 2 s |
| PEG (20%) (MW = 20,000 Da) | σ = 1.8% | No | 60 s | 8 s |
| Dextran (20%) (MW = 70,000 Da) | σ = 14.3% | No | 90 s | *N/A |
| Gelatin (300 bloom) | σ = 2.0% | **Yes (T > 60 C.) | 200+ s | 5 s |
| Paraffin Wax | σ = 2.5% | Yes (T > 60 C.) | Indefinite | Indefinite |

Note:
*denotes that test was not attempted because spotting was too inconsistent
a. **denotes that controlled release was in the diffusion limited case only Temperature control was an integral factor in successfully spotting the paraffin wax. In one exemplary embodiment, a sufficiently thick layer of paraffin (>30 μms) was required to completely protect the primers underneath during sample loading. To achieve sufficient thickness, the temperature had to be kept above the paraffin melting temperature of 37° C. to keep the solution viscous, but below 50° C. where the paraffin solution would easily wet out on the surface of the COP spreading the wax layer outside the bounds of the traps compromising the surrounding bonding surface. The pin has to be completely free floating or damage can occur during contact with the stage. In one embodiment, a "pick and place" technique where a solid pin would be dipped in a hot wax bath (by way of example and without limitation, T=100° C.) and when retracted would retain a dollop of wax, slightly larger than the pins outer diameter. The pin would then make contact with the substrate held at 42° C. (closely above the wax melting temp of 37° C.) and the wax would melt with a viscosity that resulted in a sufficiently think mound covering the primer spot.

Reagent Integration and Controlled Release

Figure 10:
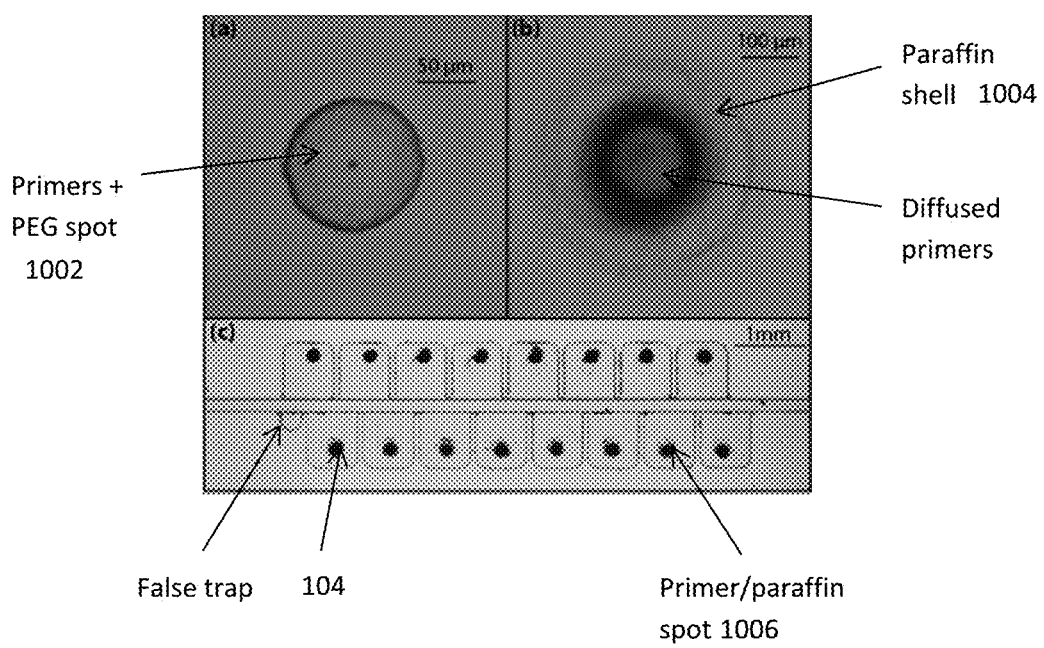
FIG. 10A is an image of a dried down PEG/primer spot.
FIG. 10B is an image of a PEG/primer spot covered by a paraffin wax capping layer.
FIG. 10C is an image of primer spots capped with paraffin in the SLD chip of FIG. 8A.

In one embodiment, PEG was included as an additive to the primer solution. By way of example and without limitation, PEG concentration may be 20% (w/w). The PEG served to improve the long term stability of the dried down oligomers as well as increase the viscosity of the spotting solution, reducing spot variability. Additionally, when dried down, the PEG additive crystallized into a solid which served as a way of visualizing the primers so that proper alignment with the subsequent wax deposition could be easily characterized. In one exemplary embodiment, as illustrated in FIG. 10A, using a 300 μm diameter pin tip with PEG 20% (w/w) mixed with primer resulted in a nominal spot size of 113.5 μm (standard deviation σ=2.1 μm). The spot 1002 had a contact angle of 45° with the COP film resulting in an estimated deposited volume of approximately 0.2 nL.

Paraffin wax was used as a capping layer 1004 for the PEG/primer spot. Using a 200 μm diameter pin resulted in a nominal paraffin wax spot size of 249.4 μm (standard deviation σ=6.3 μm) as shown in FIG. 10B. As demonstrated in FIG. 10C, paraffin capped primers were spotted into the upper center 1006 of the traps because that was the center of the reaction volume that was captured during loading. The paraffin provided a robust protective layer overtop the primers preventing rehydration during several repeated flushes with Methanol, Isopropanol and DI water though the device.

Figure 11:
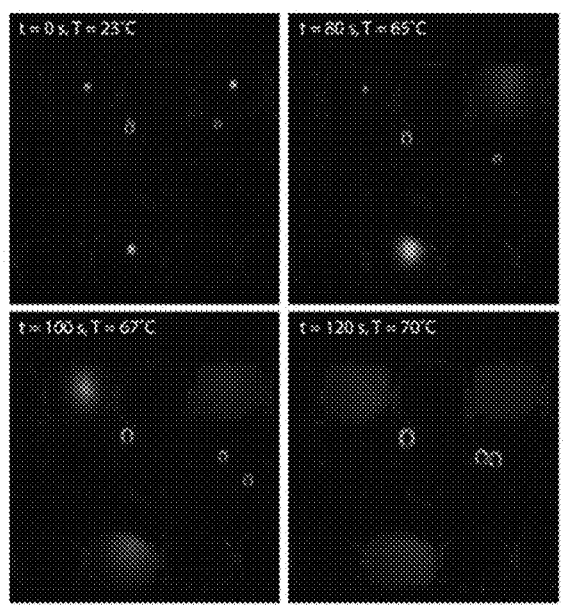
FIG. 11 is an image sequence demonstrating a temperature controlled release of fluorescein salt mixed with primer and PEG printing solution.

FIG. 11 illustrates release of the incorporated primers by adding fluorescein salt to the primer solution. The chip was loaded and backfilled with oil with no measurable difference in the fluorescence of the spots. Images were then taken as the chip was heated up to 70° C. showing the fluorescence dispersing from the original spots as the temperature reaches ~65° C.

Proper self-loading of the SLD chip, as shown in FIG. 8A, relies on the surface interactions of the sample solution and the chip substrate. A model of surface tension driven trap loading was discussed with reference to FIGS. 2A-2D, 2F, 3A-3D, 3F, and 4A-4D, 4F. However, in order to integrate PCR reagents into the sample traps, a hydrophobic material (paraffin wax) is deposited on the surface of the traps resulting in a deviation in loading percentage from the results as discussed above with reference to FIGS. 2A-2D, 2F, 3A-3D, 3F, and 4A-4D, 4F. After incorporating the paraffin spots, aqueous sample solution would circumvent the hydrophobic wax surface and leave behind an air bubble in the traps over the paraffin mounds. To overcome this deficiency, the depth of the channels was increased such that a lesser pressure change would be required to overcome the hydrophobic wax mound. Trap depth had to be limited however because self-loading and sheer induced separation during purging would be negatively impacted by increasing the depth of the channel. In one embodiment, a trap depth of 250 μm was found to be the optimum for reliable bubble free loading while also providing sufficient sample retention during purging. Trap dimensions of 900 μm (wide)×900 μm (long)×250 μm (deep) resulted in a mean captured volume of 92 nL (RSD=9.2%). Digitized volume was extrapolated by using image analysis to measure the surface area of the captured sample and multiplying it by the depth of the trap.

Multiplex PCR

The ability to detect different template DNA based on the specific integrated primer sets was important in proving the utility of the SLD chip as discussed above with reference to FIGS. 1A, 7A, and 8A for potential use in bacterial species identification and antibiotic resistance screening. Primer sets were designed to demonstrate two scenarios: 1) primer sets compatible with template would amplify while non-compatible primers would not, 2) if both primer sets would amplify with the loaded template then their respective melt temperatures (Tm) could be distinguished during an on-chip high resolution melting analysis (HRMA). To accomplish the first scenario two primer sets p19 and p322 were designed such that the p19 primer set would amplify plasmid pUC19 template and the p322 primer set would not. For the second scenario it was insured that p19 would also amplify with plasmid pBR322 template so when loading pBR322 template both p19 and p322 primer sets would be amplified, but yield amplicons with differing melt temperatures.

In one exemplary embodiment, the pUC19 and pBR322 plasmids were diluted to 30 ng/μL. Each template was mixed with equal volumes of commercial master mix and EDTA buffer to form sample solution with a final concentration of 10 ng/μL, or approximately 2.0 ng per reaction. The mastermix included LCGreen, a DNA-intercalating dye, to enable on-chip fluorescence detection of PCR reaction product and high resolution melt analysis (HRMA) for product validation. The pUC19 forward primer (5'-GACCTA-CACCGAACTGAGATACC-3') (SEQ ID NO: 1) and reverse primer (5'-TCCGACCCTGCCGCTTAC-3') (SEQ ID NO: 2) as well as pBR322 forward primer (5'-TGCT-CAACGGCCTCAACCTA-3') (SEQ ID NO: 3) and reverse primer (5'-AGTCATAAGTGCGGCGACGA-3') (SEQ ID NO: 4) were designed. In one embodiment, Primer3Plus software was used to design the primers. Both primer sets were diluted to form stock solutions at 5 mM. The primer printing solution contained 10×5 mM primer stock, 2× buffer (Novella Oligo Dilution Buffer, Canon US Life Sciences, Rockville, Md.) and 3×50% PEG solution, for a final primer concentration of 500 μM in the reaction volume.

FIG. 12A is an illustration summarizing the expected experimental outcomes. The p19 primers and pBR322 template produced an amplicon with similar Tm as the p19 primer and pUC19 template. In one embodiment, both primer sets were designed to amplify under the same thermocycling conditions—20 cycles of 95° C. for 15 s, 60° C. and 72° C. for 30 s. By way of example and without limitation, the assay was run on a Roche LC480 beforehand and HRMA confirmed that the p19 primers and pBR322 template reaction yielded amplicons that had a Tm 2.3° C. lower than the amplicons produced by p322 primers and pBR322 template.

The SLD chip was designed to minimize workflow such that only two pipetting steps (one for sample and one for oil)

is all that is required to discretize a sample into separate reactions. This was realized experimentally with a 16 trap device loaded in less than 60 s. A trap loading percentage of 75% and 100% for pUC19 template and pBR322 template loaded chips, respectively, was achieved. HRMA showed that the traps filled with p19 produced an amplicon with a mean Tm=86.4° C. (standard deviation σ=0.3° C.). The chip loaded with pBR322 template loaded all traps successfully. Traps filled with the p19 primers amplified a product with a mean Tm=87.3° C. (standard deviation σ=0.7° C.), and traps filled with the p322 primers produced an amplicon with a mean Tm=89.5° C. (standard deviation σ=0.7° C.). A difference in the Tm of 2.2° C. between p19/pBR322 and p322/pBR322 amplicons is in good agreement with the difference in amplicon Tm measured on the LC480.

The need for sample preparation presents a significant challenge toward any nucleic acid diagnostic designed for use at the point-of-care. In one embodiment of the present invention, sample preparation is decoupled from the microfluidic amplification and SLD detection platform, allowing the process of nucleic acid extraction, purification, and concentration to be modified for specific sample types while maintaining a universal microfluidic platform for back-end analysis. Specifically, the sample preparation is performed using functionalized pipette tips. An example of workflow is depicted in FIGS. 13A-13C, where the custom pipette tip takes advantage of chitosan functionalization of porous polymer monoliths used for DNA capture and release.

As depicted in FIG. 13A, raw sample is drawn through a chitosan monolith, where charge interactions capture free nucleic acids on the porous surface. A pre-filter element integrated into the tip also serves to remove particles and cell debris from the sample. In one embodiment, the pre-filter element is a chitosan monolith 1302. Specifically, 1 mm thick chitosan monolith element 1302 is sufficient to capture DNA with loading levels over 100 ng per square millimeter of monolith area. After capture, the sample is washed with pH 5 buffer to remove contaminants (FIG. 13B), after which amplification buffer at pH 8.8 was loaded into the pipette and used to elute concentrated DNA directly into the trap chip (FIG. 13C). In yet another embodiment, this process is simplified by using a syringe rather than a pipette, with rinse and elution buffers preloaded into the syringe body.

Accordingly, in addition to decoupling sample preparation and amplification in a process that is tractable for use at the point of care, this approach also eliminates the need for chaotropic salts for DNA concentration and purification, solves the world-to-chip interface challenge, and enables reliable control over sample volume during nucleic acid elution without the need for complex or bulky instrumentation.

Multiplexed assays using nucleic acid amplification offer particular potential in point-of-care settings where the ability to rapidly detect multiple biomarkers with high specificity and sensitivity can have a transformative effect on healthcare. However, established PCR-based nucleic acid diagnostics require significant instrumentation to support multiplexing, making them too cumbersome, costly, and difficult to use at the point of care. Furthermore, conventional PCR is too slow for many point-of-care applications.

According to one aspect of the present invention, a microfluidic platform is provided to overcome these limitations and use multiplexed nucleic acid diagnostics in point-of-care settings. The platform employs a thermoplastic chip designed to automatically segregate an initial sample volume into large numbers of isolated reaction chambers containing all reagents necessary for multiplexed amplification and detection, without the need for any external pumps or valves, substrate preparation, or reagent introduction. Simultaneous on-chip amplification is achieved by using loop-mediated isothermal amplification (LAMP), greatly simplifying the system-level multiplexing requirements. Significantly, through the use of contact imaging, the system is exceptionally compact, ultimately allowing all functions to be integrated into a USB stick format that supports assay operation and readout using a notebook or tablet computer.

LAMP operates at 60-65° C. and exponentially amplifies DNA sequences through the formation of loops in the amplicons, enabling primer binding without DNA melting. In addition to exponential amplification, the method is rapid because of the elimination of the thermal cycling time as well as the continued evolution of the Bst polymerase.

Figure 16:
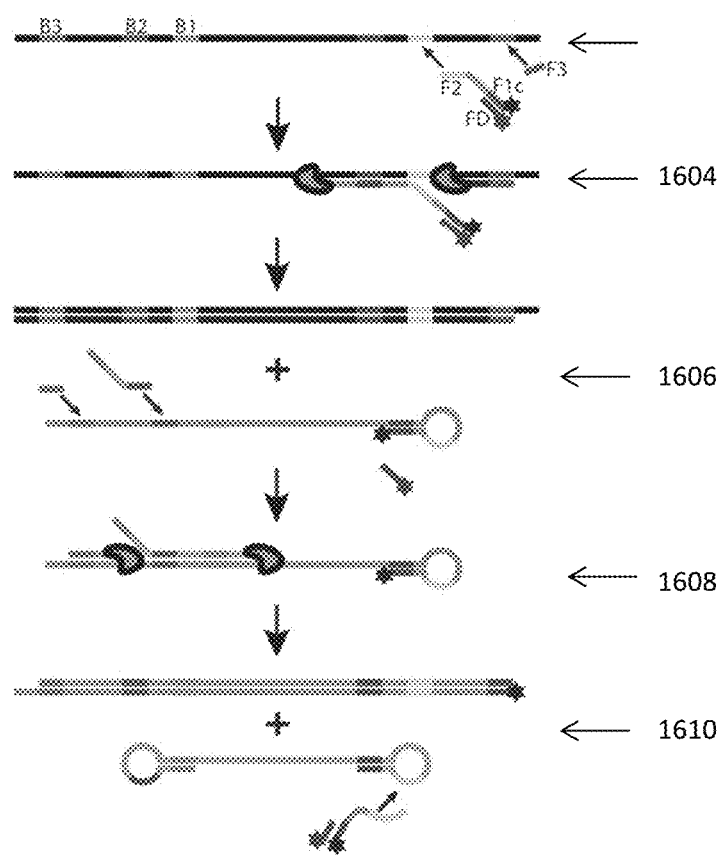
FIG. 16 illustrates a loop-mediated isothermal amplification (LAMP) reaction scheme.

Amplification reactions can reach saturation in as fast as ten minutes. For increased specificity, the LAMP reaction (Tanner et al., "Simultaneous multiple target detection in real-time loop-mediated isothermal amplification," Biotechniques, vol. 53, no. 2, pp. 81-89, 2012) is demonstrated in FIG. 16. Following the initial melt step, the primers F2 and F3 bind to the target, step 1602. F2 has attached to it F1c, which is hybridized with FD; FD contains a donor fluorophore while F1c contains a quencher. In step 1604, polymerase binding at F2 will extend a complement to the template, while polymerase that binds at F3 will also extend the template while displacing the other strand. As the strand is displaced, a loop is formed by the self-hybridization at F1; this loop formation also displaces FD, which leads to an increase in fluorescence, step 1606. Next, a similar process occurs in the reverse direction at B1c, B2c, and B3c, step 1608. Ultimately, this first round of copying generates strands with loops on each end, step 1610. The loops enable primer access without further DNA melts, thus leading to the repeated copying of these loop-based structures at an exponentially increasing rate. Signal is also generated at an exponentially increasing rate due to the continued displacement of FD strands at each copying of the loop structures.

In one exemplarily embodiment, a disposable thermoplastic microfluidic chip supporting multiplexed LAMP assays is fabricated in COP substrate with a high density array of up to 1024 reaction chambers (by way of example and without limitation, 32×32 wells, 100 nL volume) in a footprint below 2.5 cm². Lyophilized LAMP reagents, including Bst polymerase and target-specific primers, are integrated on-chip by microarray spotting in a wax matrix to enable controlled release of reagents. Thin film platinum heaters and thermistors supporting precise temperature control are patterned on the chip surface.

Accordingly, a simple, automated, and disposable platform capable of rapidly amplifying up to 1024 independent gene targets using spatially multiplexed isothermal amplification is uniquely suited for near-patient settings.

A key advance of the present invention is the development of on-chip multiplexed LAMP as an isothermal amplification technique. In contrast to PCR, LAMP reactions are performed at a constant temperature, eliminating the need for rapid thermocycling. Thus, moving to isothermal amplification greatly simplifies system-level operation of the devices to allow for USB integration. The lower temperatures associated with LAMP amplification (typically 60-65° C.) serves to reduce the impact of thermally-induced bubble formation. Furthermore, because each LAMP reaction employs multiple primers to identify distinct regions on the target gene, specificity is greatly enhanced over PCR, while the addition of loop primers accelerates the reaction, allowing amplicons to be generated at a higher rate than PCR for assay times.

Figure 15:
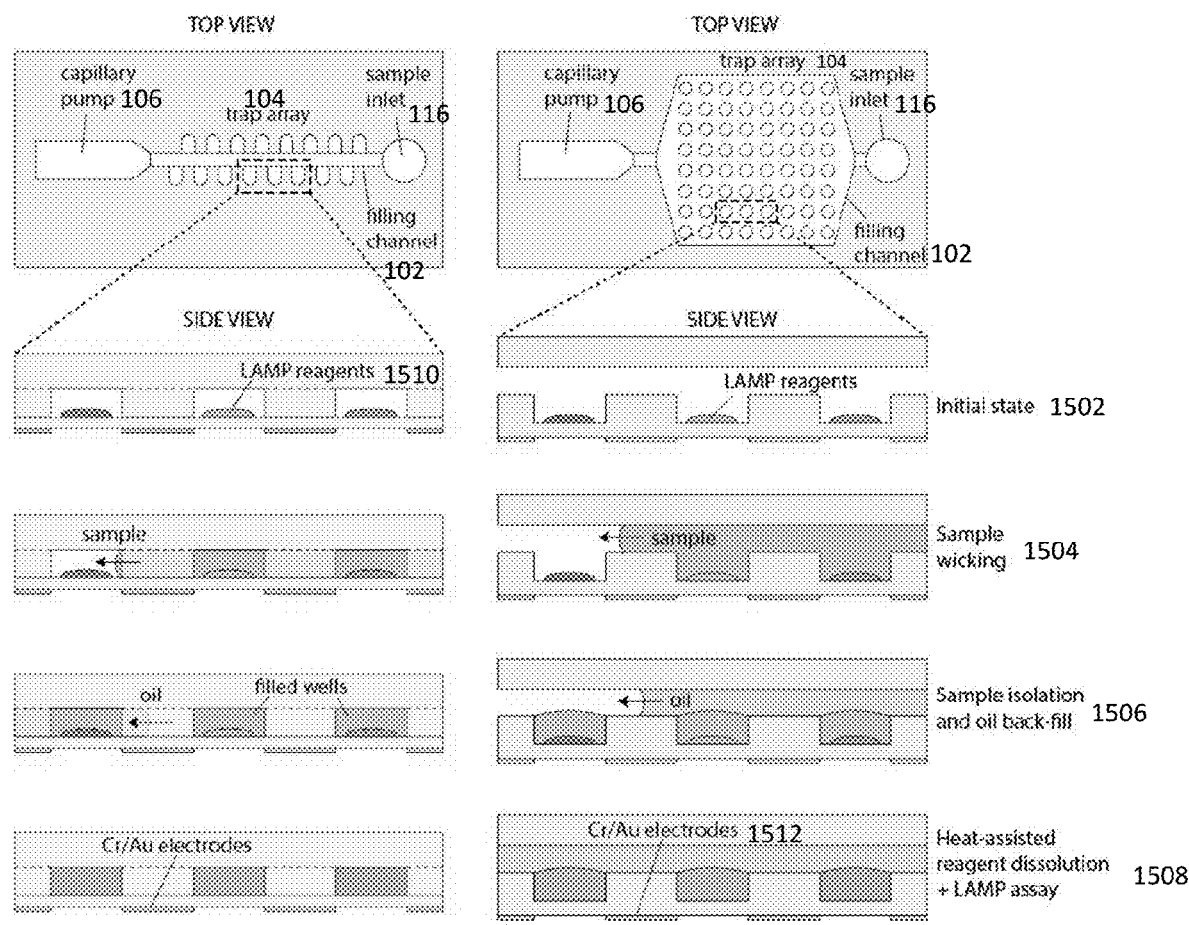
FIGS. 15A-15B illustrate comparison of the staggered trap design (FIG. 15A) to the planar vertical trap design (FIG. 15B).

While the staggered trap array, as demonstrated in FIG. 7A, successfully enabled automated sample filling and discretized PCR, progress was limited due to fabrication challenges relating to chip bonding. In one aspect of the present invention, a new array design in which the sample traps are fabricated as vertical wells beneath a planar microchannel, rather than lateral protrusions emerging from the sides of a single linear microchannel. FIGS. 15A-15B demonstrate comparison of the staggered trap design (FIG. 15A) to the planar vertical trap design (FIG. 15B). Each chip, as shown in FIGS. 15A-15B, comprises a sample inlet 116, a filling channel 102, a trap array 104, and a capillary pump 106.

Initial state 1502 demonstrates two trap array configurations prior to receiving the sample at the sample inlet 116. The staggered trap design is shown in FIG. 15A and the planar vertical trap design is shown in FIG. 15B. Each sample trap (well) 104 contains LAMP reagents 1510 for performing an amplification reaction. Cr/Au electrodes 1512 are attached to the chip. A sample is introduced through the sample inlet port 116 and fills the sample traps 104, step 1504. After an excess sample has been removed by the integrated capillary pump (PVDF membrane) 106, the oil is introduced into the channel 102 to isolate the sample traps, step 1506. In step 1508, Cr/Au electrodes 1512 provide for heat-assisted release of LAMP reagents to amplify target nucleic acids in the sample.

Vertical trap filling process is demonstrated in FIG. 14. In one embodiment, effective loading of square traps with in-plane dimensions ranging from 50 μm to 250 μm and heights ranging from 50 μm to 100 μm have been successfully demonstrated, with sample filling and discretization during oil backfill achieved. Filling of the chips is facilitated by activation of the thermoplastic surface containing the microwells through exposure to UV/ozone, generating in a dense layer of negatively charged groups on the surface, resulting in high surface energy and promoting hydrophilic anchoring of discrete sample volumes within the traps during oil backfill. The use of surface activation also significantly enhances the speed of the filling process over staggered trap arrays due to higher capillary forces in the hydrophilic devices. In one embodiment, a staggered trap array concept may be adapted to the vertical trap design by patterning a second set of staggered 2D traps on the opposing channel surface to increase the achievable trap volume.

Because the wells in the vertical design are located far from the bond interface, bubble formation does not impact amplification or assay readout, allowing the use of robust solvent bonding methods for high chip yield, while the 2-D geometry of the filling channel allows large arrays of sample traps to be rapidly (by way of example and without limitation, <30 sec) filled from a single inlet port. Avoiding the high temperatures necessary in PCR allows for reducing thermally induced bubble formation.

To enable multiplexed amplification, target-specific LAMP primers and polymerase are deposited by mechanical spotting in individual trap chambers, and controllably released during an initial LAMP heating step. An effective technique is provided for depositing PCR primers in a PEG matrix, with paraffin wax encapsulation supporting thermally-controlled reagent release, thereby preventing primer cross-talk between traps during sample filling (FIG. 10A-10C).

In one exemplarily embodiment, the combination of the planar vertical trap chip design and reagent spotting allows for achieving a 32×32 array of 1024 traps containing integrated reagents. Trap chamber has dimensions of 500 μm diameter and 500 μm height for a well volume of approximately 100 nL, and a total sample volume of ~100 μL for the entire array. This array design resides within a 2.5 cm² footprint, allowing optical detection from the full array using a simple contact imaging system integrated into a USB stick.

Figure 18:
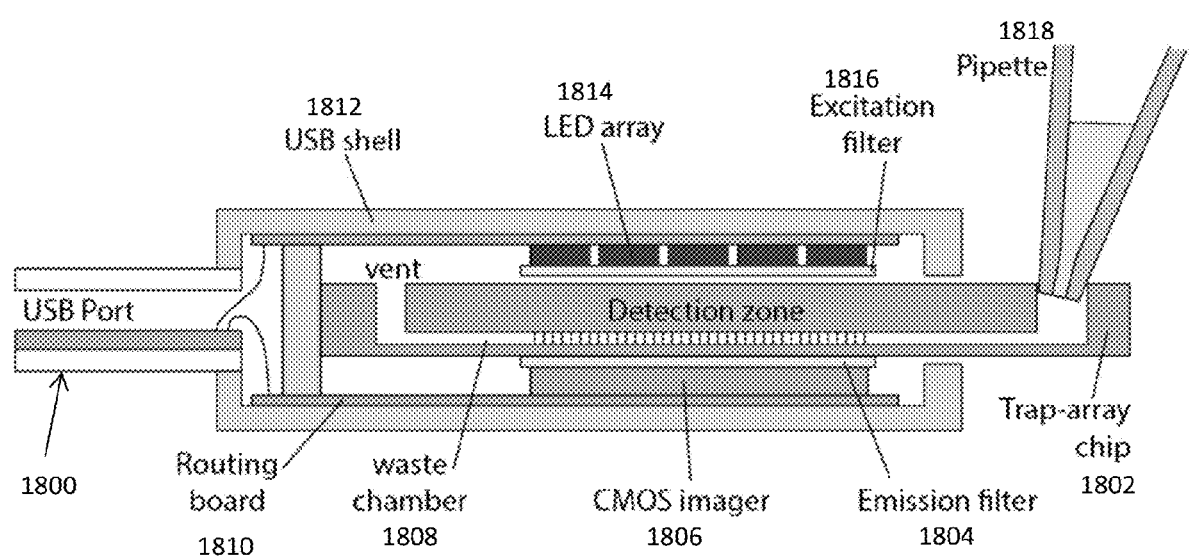
FIG. 18 illustrates a reusable CMOS contact fluorescence system integrated into a USB stick.

A reusable CMOS contact fluorescence system 1806 integrated into a USB stick 1800 along with a trap-array chip 1802 and LED array 1814 is demonstrated in FIG. 18. The external thermoelectric (for example a thermocycler) used for temperature control in SLD chips is replaced with integrated thin film Cr/Au electrodes, significantly reducing power requirements for the devices. Specifically, Cr/Au electrodes (element 1512 in FIGS. 15A-15B) are patterned on the chip backside for temperature sensing and actuation. The electrodes are positioned in the periphery of each trap to avoid blocking optical access from either the top or bottom chip surfaces. All interface electronics is implemented on a single printed circuit board 1810 using a stamp-sized microcontroller.

Fluorescence imaging of the trap-array 1802 is performed using front-side LED illumination 1814 and back-side detection using the CMOS contact imager 1806, obviating the need for any optical focusing components in the system. By placing the CMOS imager 1806 in close proximity to the imaging surface, high-resolution optical detection can be achieved. An excitation filter glass 1816 is placed between the LED source 1414 and trap-array chip 1802, while an emission filter glass 1804 is placed between the trap-array chip and CMOS detector 1806.

The realization of a rapid multiplexed diagnostic operated from a laptop computer, without the need for any external instrumentation, opens the door to environments ranging from small clinics, individual doctor offices, remote settings with limited access to conventional laboratory infrastructure or other resources, and ultimately in-home use. To this end, a CMOS chip supporting a standard SPI (I2C) interface can be employed to simplify USB communication, with Java code on the host computer used for SPI control and data collection from the imager, together with control of the LED light sources 1814 and thin film temperature control elements.

Figure 17:
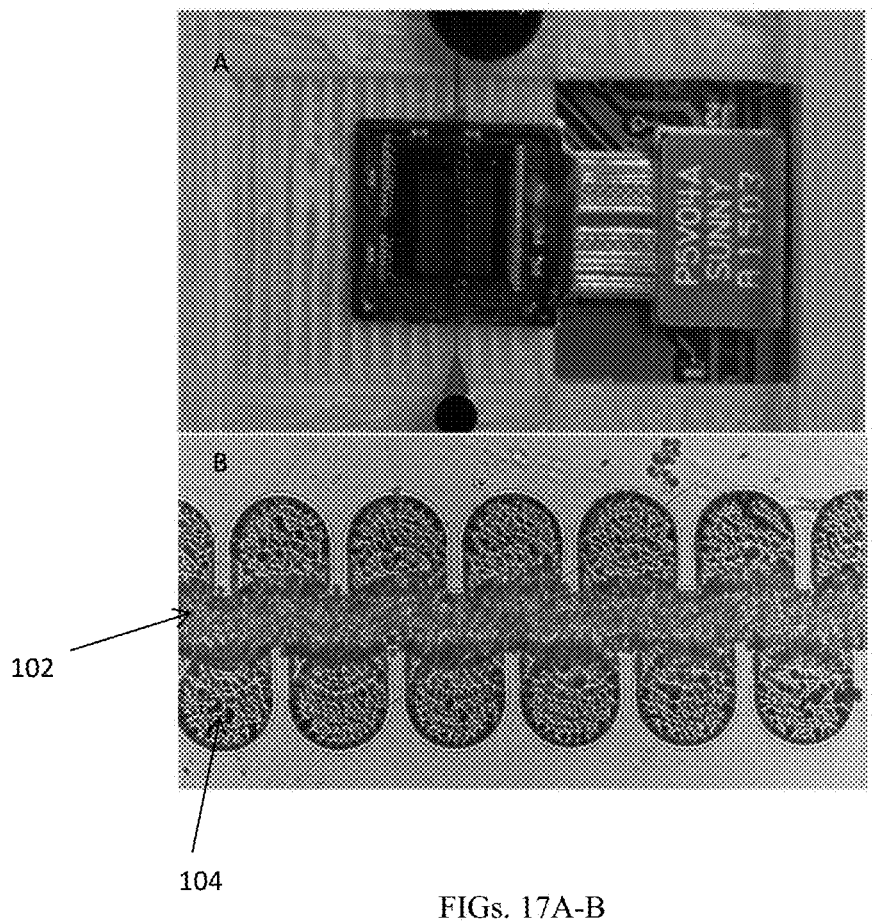
FIG. 17A illustrates a CMOS imager positioned below a trap chip.
FIG. 17B illustrates contact imaging results using fluorescent dye.

High fidelity fluorescence images are achieved using a bare consumer-grade CMOS imager chip as shown in FIGS. 17A-17B. FIG. 17A demonstrates a bare CMOS imager positioned below a trap chip. FIG. 17B demonstrates contact imaging results using fluorescent dye. Fluorescence signal detected at each trap 1704 and the channel 1702 is filled with oil are shown in FIG. 17B.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use

We claim:

1. A method comprising:
providing a substrate having a first microfluidic channel provided therein, the first microfluidic channel being in fluid communication with an inlet port and an outlet port and a plurality of sample traps branching directly off the first microfluidic channel, wherein a second microfluidic channel is in fluid communication with an immiscible fluid inlet port and a plurality of immiscible fluid outlet ports, and wherein between the immiscible fluid inlet port and the immiscible fluid outlet ports the second microfluidic channel is in fluid communication with each of the plurality of sample traps which are arranged in rows on both sides of the second microfluidic channel, such that at least a portion of the first and second microfluidic channels are parallel to each other with the plurality of sample traps disposed therebetween,
wherein the first microfluidic channel connects the inlet port to a capillary pump with the sample traps in between, wherein a sealing layer is bonded to the substrate;

introducing a sample into the first microfluidic channel through the inlet port, wherein the sample is self-filled into the sample traps;

removing an excess sample from the first microfluidic channel by the capillary pump;

introducing an immiscible fluid into the second microfluidic channel through the immiscible fluid inlet port;

filling the second microfluidic channel with an immiscible fluid, wherein the immiscible fluid isolates the sample traps; and wherein each of the plurality of traps has geometrical parameters selected to optimize self-filling of the sample traps with the sample via pinning, wherein an advancing fluid front of the sample will be pinned to one or more surfaces of the channel, such that the advancing fluid front will expand beyond a critical angle causing the sample to enter a sample trap.

2. The method of claim 1, wherein the geometrical parameters include a channel width, a trap width, a trap depth, a channel height, and a trap height.

3. The method of claim 1, wherein the sample traps branch off from the same side of the first microfluidic channel.

4. The method of claim 1, wherein the sample traps branch off from both sides of the first microfluidic channel.

5. The method of claim 1, wherein the sample traps branch off from both sides of at least a portion of the first microfluidic channel and are centerline offset.

6. The method of claim 1, wherein the sealing layer is a thin film layer.

7. The method of claim 6, wherein the thickness of the thin film layer is 200 µm.

8. The method of claim 1, wherein each sample trap comprises pre-deposited reagents.

9. The method of claim 8, wherein the pre-deposited reagents are integrated into each sample trap during fabrication to perform a different reaction within each sample trap.

10. The method of claim 8, wherein the pre-deposited reagents are loop-mediated isothermal amplification (LAMP) reagents including primers to amplify target nucleic acids in the sample, the LAMP reagents encapsulated into a paraffin wax ensuring that the LAMP reagents remain encapsulated during sample introduction.

11. The method of claim 8, wherein the pre-deposited reagents are polymerase chain reaction (PCR) reagents including primers to amplify target nucleic acids in the sample, the PCR reagents encapsulated into a paraffin wax ensuring that the primers remain encapsulated during sample introduction.

12. The method of claim 11, wherein the primers are released from the paraffin wax by temperature application prior to thermocycling.

13. The method of claim 1, wherein the capillary pump is an absorbent membrane.

14. The method of claim 13, wherein the absorbent membrane is a polyvinylidene fluoride (PVDF) membrane.

15. The method of claim 1, wherein the sample is injected into the inlet port by a pipette.

16. The method of claim 1, wherein the trap has dimensions of 900 µm (wide)×900 µm (long)×250 µm (deep).

17. The method of claim 1, wherein the immiscible fluid is silicone oil.

18. The method of claim 1, wherein the substrate is fabricated from a thermoplastic polymer.

19. The method of claim 1, wherein the substrate is fabricated from thermoplastic cyclic olefin polymer (COP).

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: pUC19 forward primer

<400> SEQUENCE: 1
gacctacacc gaactgagat acc                                              23

<210> SEQ ID NO 2
<211> LENGTH: 18
<212> TYPE: DNA
<213> ORGANISM: Artificial Sequence
<220> FEATURE:
<223> OTHER INFORMATION: pUC19 reverse primer

<400> SEQUENCE: 2
tccgaccctg ccgcttac                                                    18

<210> SEQ ID NO 3
<211> LENGTH: 20
<212> TYPE: DNA
<213> ORGANISM: Artificial Sequence
<220> FEATURE:
<223> OTHER INFORMATION: pBR322 forward primer

<400> SEQUENCE: 3
tgctcaacgg cctcaaccta                                                  20

<210> SEQ ID NO 4
<211> LENGTH: 20
<212> TYPE: DNA
<213> ORGANISM: Artificial Sequence
<220> FEATURE:
<223> OTHER INFORMATION: pBR322 reverse primer

<400> SEQUENCE: 4
agtcataagt gcggcgacga                                                  20